(12) United States Patent
Contreras et al.

(10) Patent No.: US 11,759,576 B2
(45) Date of Patent: Sep. 19, 2023

(54) PARENTERAL INJECTION APPARATUS

(71) Applicant: Action Medical Technologies, LLC, Conshohocken, PA (US)

(72) Inventors: Andrew D. Contreras, Fairfax Station, VA (US); Mark W. Pursel, Grantville, PA (US); Joseph B. Hoffer, Newport, PA (US)

(73) Assignee: ACTION MEDICAL TECHNOLOGIES, LLC, Conshohocken, PA (US)

( * ) Notice: Subject to any disclaimer, the term of this patent is extended or adjusted under 35 U.S.C. 154(b) by 284 days.

(21) Appl. No.: 17/340,246

(22) Filed: Jun. 7, 2021

(65) Prior Publication Data

US 2021/0379292 A1 Dec. 9, 2021

Related U.S. Application Data

(60) Provisional application No. 63/128,496, filed on Dec. 21, 2020, provisional application No. 63/035,277, filed on Jun. 5, 2020.

(51) Int. Cl.
*A61M 5/315* (2006.01)
*A61M 5/32* (2006.01)

(52) U.S. Cl.
CPC .... *A61M 5/31585* (2013.01); *A61M 5/31515* (2013.01); *A61M 5/32* (2013.01)

(58) Field of Classification Search
CPC ...... A61M 5/42; A61M 5/46; A61M 25/0612; A61M 25/0625; A61M 2005/1581; A61M 5/31585; A61M 5/31515; A61M 5/32
See application file for complete search history.

(56) References Cited

U.S. PATENT DOCUMENTS

| | | |
|---|---|---|
| 3,572,336 A | 3/1971 | Hershberg |
| 3,742,948 A | 7/1973 | Post et al. |
| 4,031,893 A | 6/1977 | Kaplan et al. |
| 4,447,231 A | 5/1984 | Bekkering |
| 4,529,403 A | 7/1985 | Kamstra |
| 4,559,043 A | 12/1985 | Whitehouse et al. |
| 4,767,416 A | 8/1988 | Wolf et al. |
| 4,998,924 A | 3/1991 | Ranford |
| 5,271,744 A | 12/1993 | Kramer et al. |
| 5,320,609 A | 6/1994 | Haber et al. |
| 5,478,316 A | 12/1995 | Bitdinger et al. |
| 5,637,094 A | 6/1997 | Stewart et al. |
| 5,957,896 A | 9/1999 | Bendek et al. |
| 6,159,181 A | 12/2000 | Crossman et al. |
| 6,319,234 B1 | 11/2001 | Restelli et al. |
| 6,699,224 B2 | 3/2004 | Kirchhofer et al. |
| 6,808,507 B2 | 10/2004 | Roser |
| 7,381,201 B2 | 6/2008 | Gilbert et al. |
| 7,517,334 B2 | 4/2009 | Jacobs et al. |

(Continued)

FOREIGN PATENT DOCUMENTS

CN 102497899 A 6/2012
CN 102665801 A 9/2012

(Continued)

*Primary Examiner* — Dung T Ulsh
(74) *Attorney, Agent, or Firm* — Duane Morris LLP

(57) ABSTRACT

The disclosure relates to a parenteral injection apparatus that guides a needle of an injector into a target site to deliver medicaments and other fluids.

15 Claims, 23 Drawing Sheets

(56) References Cited

U.S. PATENT DOCUMENTS

| | | |
|---|---|---|
| 7,717,877 B2 | 5/2010 | Lavi et al. |
| 7,905,352 B2 | 3/2011 | Wyrick |
| 7,931,618 B2 | 4/2011 | Wyrick |
| 8,123,724 B2 | 2/2012 | Gillespie, III |
| 8,187,224 B2 | 5/2012 | Wyrick |
| 8,313,463 B2 | 11/2012 | Barrow et al. |
| 8,343,103 B2 | 1/2013 | Moser |
| 8,460,245 B2 | 6/2013 | Guillermo et al. |
| 8,491,530 B2 | 7/2013 | Maritan |
| 8,529,499 B2 | 9/2013 | Matusch |
| 8,529,510 B2 | 9/2013 | Giambattista et al. |
| 8,679,061 B2 | 3/2014 | Julian et al. |
| 8,696,625 B2 | 4/2014 | Carrel et al. |
| 8,845,594 B2 | 9/2014 | Jennings |
| 9,017,293 B2 | 4/2015 | Edhouse et al. |
| 9,044,553 B2 | 6/2015 | James et al. |
| 9,186,459 B2 | 11/2015 | Bechmann et al. |
| 9,216,256 B2 | 12/2015 | Olson et al. |
| 9,242,044 B2 | 1/2016 | Markussen |
| 9,265,886 B2 | 2/2016 | Wyrick |
| 9,283,326 B2 | 3/2016 | Kemp et al. |
| 9,364,617 B2 | 6/2016 | Riedel |
| 9,421,337 B2 | 8/2016 | Kemp et al. |
| 9,427,531 B2 | 8/2016 | Hourmand et al. |
| 9,486,582 B2 | 11/2016 | Abry et al. |
| 9,579,471 B2 | 2/2017 | Carrel et al. |
| 9,827,381 B2 | 11/2017 | Hourmand et al. |
| 10,058,654 B2 | 8/2018 | Gabrielsson |
| 10,525,201 B2 | 1/2020 | Brunnberg et al. |
| 2001/0056263 A1 | 12/2001 | Alchas et al. |
| 2003/0036724 A1 | 2/2003 | Vetter et al. |
| 2003/0050609 A1 | 3/2003 | Sams |
| 2006/0189938 A1 | 8/2006 | Hommann et al. |
| 2010/0016793 A1 | 1/2010 | Jennings et al. |
| 2010/0298768 A1 | 11/2010 | Halili, Jr. et al. |
| 2012/0101475 A1 | 4/2012 | Wilmot et al. |
| 2012/0123350 A1 | 5/2012 | Giambattista et al. |
| 2012/0209192 A1 | 8/2012 | Alexandersson |
| 2013/0123710 A1 | 5/2013 | Ekman et al. |
| 2013/0190721 A1 | 7/2013 | Kemp et al. |
| 2013/0310759 A1 | 11/2013 | Hourmand et al. |
| 2014/0135705 A1 | 5/2014 | Hourmand et al. |
| 2014/0228769 A1 | 8/2014 | Karlsson et al. |
| 2015/0011975 A1 | 1/2015 | Anderson et al. |
| 2015/0025474 A1 | 1/2015 | Riedel et al. |
| 2015/0246181 A1 | 9/2015 | Fourt et al. |
| 2015/0250951 A1 | 9/2015 | Karlsson et al. |
| 2015/0265782 A1 | 9/2015 | Riedel et al. |
| 2015/0283323 A1 | 10/2015 | Young et al. |
| 2016/0008542 A1 | 1/2016 | Hirschel et al. |
| 2016/0008546 A1 | 1/2016 | Rekaya et al. |
| 2017/0136186 A1 | 5/2017 | Marsh et al. |
| 2017/0188990 A1* | 7/2017 | Von Allmen ............ A61B 5/153 |
| 2017/0274158 A1* | 9/2017 | Saeed Malik ....... A61M 5/3287 |
| 2017/0361032 A1* | 12/2017 | Kim ....................... A61M 5/42 |
| 2018/0099095 A1 | 4/2018 | Standley et al. |
| 2018/0296764 A1 | 10/2018 | Davies et al. |
| 2019/0143050 A1 | 5/2019 | Montgomery et al. |
| 2022/0273888 A1* | 9/2022 | Knight ................ A61M 5/3243 |

FOREIGN PATENT DOCUMENTS

| | | |
|---|---|---|
| CN | 103249443 A | 8/2013 |
| CN | 103945881 A | 7/2014 |
| JP | 2010532243 | 10/2010 |
| JP | 2013529521 | 7/2013 |
| JP | 2015519135 | 7/2015 |
| JP | 2015530170 | 10/2015 |
| WO | 2012000873 A1 | 1/2012 |
| WO | 2018125629 A1 | 7/2018 |

* cited by examiner

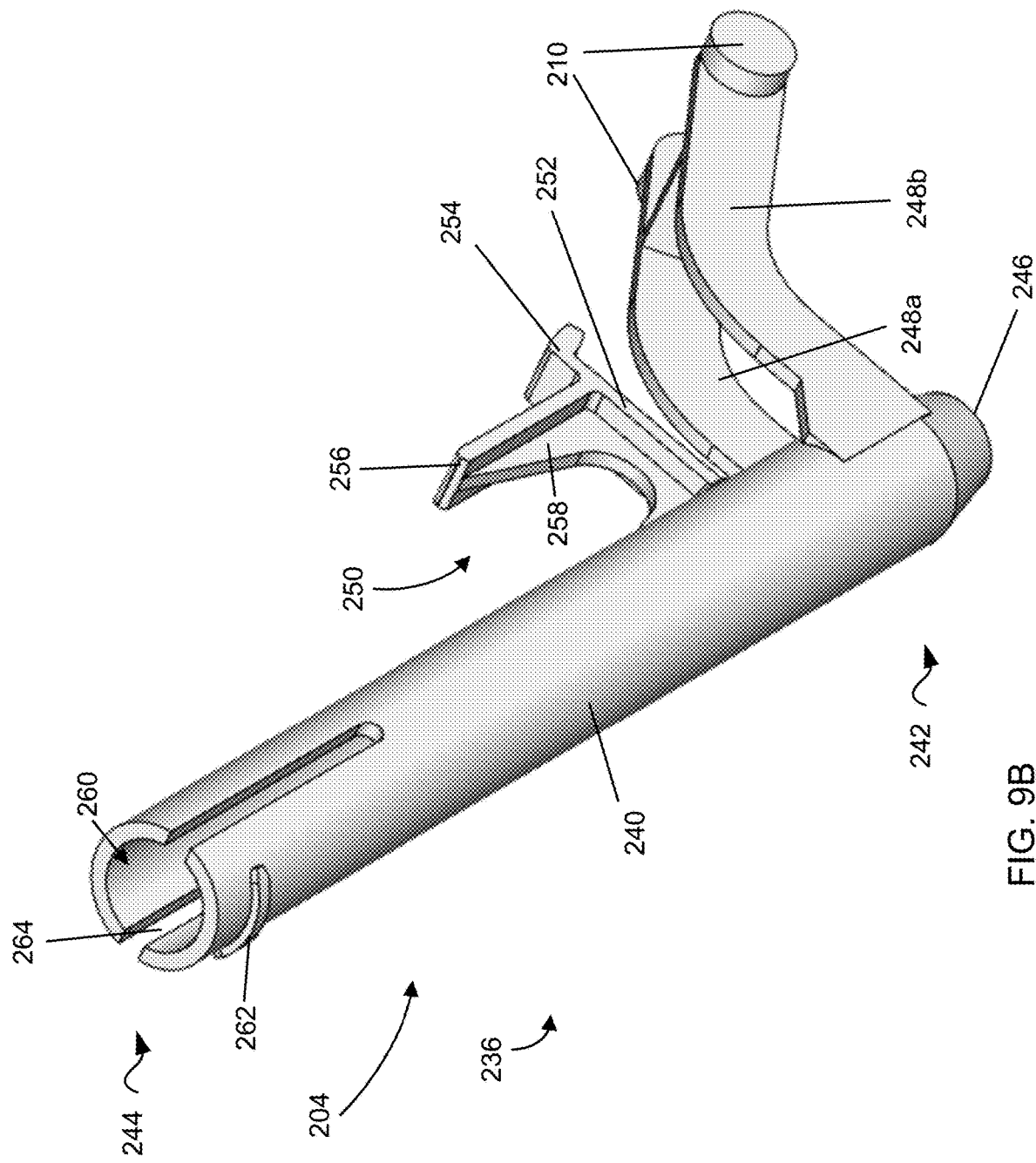

PARENTERAL INJECTION APPARATUS

CROSS REFERENCE TO RELATED APPLICATIONS

This application claims benefit of U.S. Provisional Patent Application No. 63/035,277, filed Jun. 5, 2020, and of U.S. Provisional Patent Application No. 63/128,496, filed Dec. 21, 2020, the entirety of each disclosure is incorporated by reference herein.

TECHNICAL FIELD

The present disclosure relates generally to injectors for medicaments and other fluids, and more particularly, to a parenteral injection apparatus that guides a needle of an injector into a target site.

BACKGROUND

Many methods are used to inject medicaments and other fluids into a target site of a body. These include syringes, auto-injectors, and drug pumps. The medicament can be injected at a variety of depths. For example, the medicament can be injected into the epidermis, the dermis, the subcutaneous region, or into the muscles (i.e., intramuscular). Medicament or other fluids can also be delivered intravenously, intraosseously, and/or to other parts of the body such as into the eye. An administrator, such as a health care provider, may insert the injector at a certain angle in order for the needle and the medicament or other fluid to reach the target site. For example, to perform an intradermal injection, the administrator may stretch the skin of the patient taut, insert the needle into the patient at an angle of 5°-15°, and administer the medicament or other fluid. Typically, a weal or bleb appears in the patient's skin, which indicates that the medicament is injected in the dermis. However, seeing the weal or bleb is dependent on the administrator inserting the needle at the correct angle. If the administrator mistakenly inserts the needle at the incorrect angle, the administrator may have to reinsert the needle to attempt another injection.

SUMMARY

In one or more embodiments, an injection apparatus includes a syringe housed within a sleeve. In one or more cases, the syringe includes a barrel, a needle mounted to an end of the barrel, a plunger, and a seal slidably mounted in the barrel. In some embodiments, the injection apparatus includes a housing. In some embodiments, the sleeve includes an arm that extends from the sleeve and is coupled to the housing such that the sleeve is configured to rotate within the housing and guide the needle to a target site.

In one or more embodiments, an injection apparatus includes a housing having a protruded member extending upwardly from a planar member of the housing. In some cases, the protruded member includes a cavity sized to receive a sleeve therein. In some embodiments, the sleeve is configured to receive a syringe and includes an arm that extends from the sleeve and is rotatably coupled to the housing such that the sleeve is rotatable within the housing to guide a needle of the syringe to a target site.

A variety of additional aspects will be set forth in the description that follows. The aspects can relate to individual features and to combination of features. It is to be understood that both the foregoing general description and the following detailed description are exemplary and explanatory only and are not restrictive of the broad inventive concepts upon which the embodiments disclosed herein are based.

BRIEF DESCRIPTION OF THE DRAWINGS

The following drawings are illustrative of particular embodiments of the present disclosure and therefore do not limit the scope of the present disclosure. The drawings are not to scale and are intended for use in conjunction with the explanations in the following detailed description.

FIG. 9B is a perspective view of the receiving portion.

DETAILED DESCRIPTION

Figure 1:
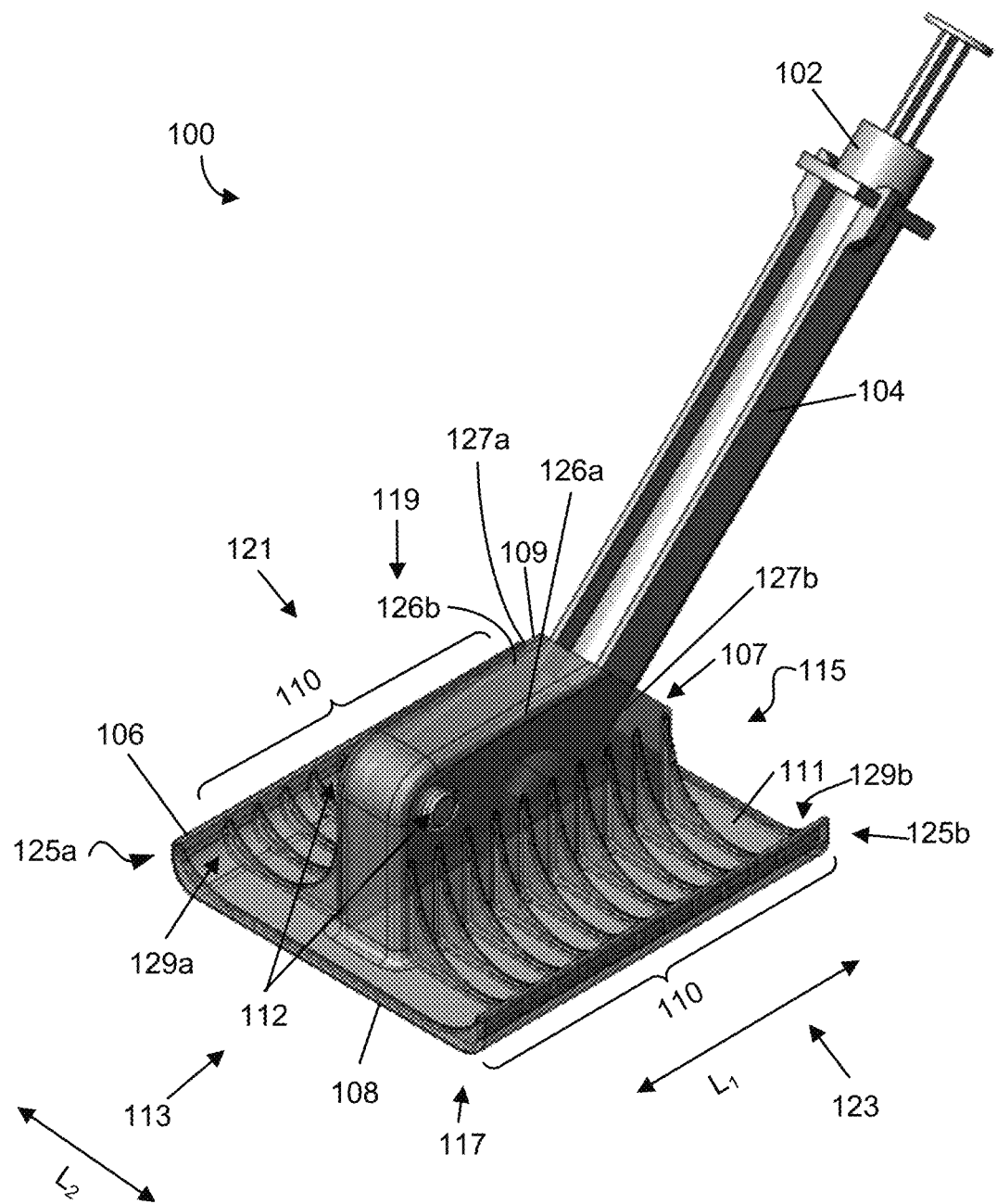
FIG. 1 is a perspective view of an example of a parenteral injection apparatus.

The following discussion omits or only briefly describes conventional features of injectors that are apparent to those skilled in the art. It is noted that various embodiments are described in detail with reference to the drawings, in which like reference numerals represent like parts and assemblies throughout the several views. Reference to various embodiments does not limit the scope of the claims attached hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest reasonable interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "includes" and/or "including," when used in this specification, specify the presence of stated features, elements, and/or components, but do not preclude the presence or addition of one or more other features, steps, operations, elements, components, and/or groups thereof. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively or operably connected" is such an attachment, coupling or connection that allows the pertinent structures to operate as intended by virtue of that relationship. The terms "medicament" or "fluid" as used herein refers to any substance for delivery to a target. For example, these terms include anticoagulants, vaccines, biologics, or any other injectable fluids.

Embodiments of the present disclosure relate generally to injectors for medicaments and other fluids, and more particularly, to a parenteral injection apparatus that guides a needle of an injector into a target site. Embodiments of the parenteral injection apparatus are described below with reference to FIGS. 1-11B.

Figure 2:
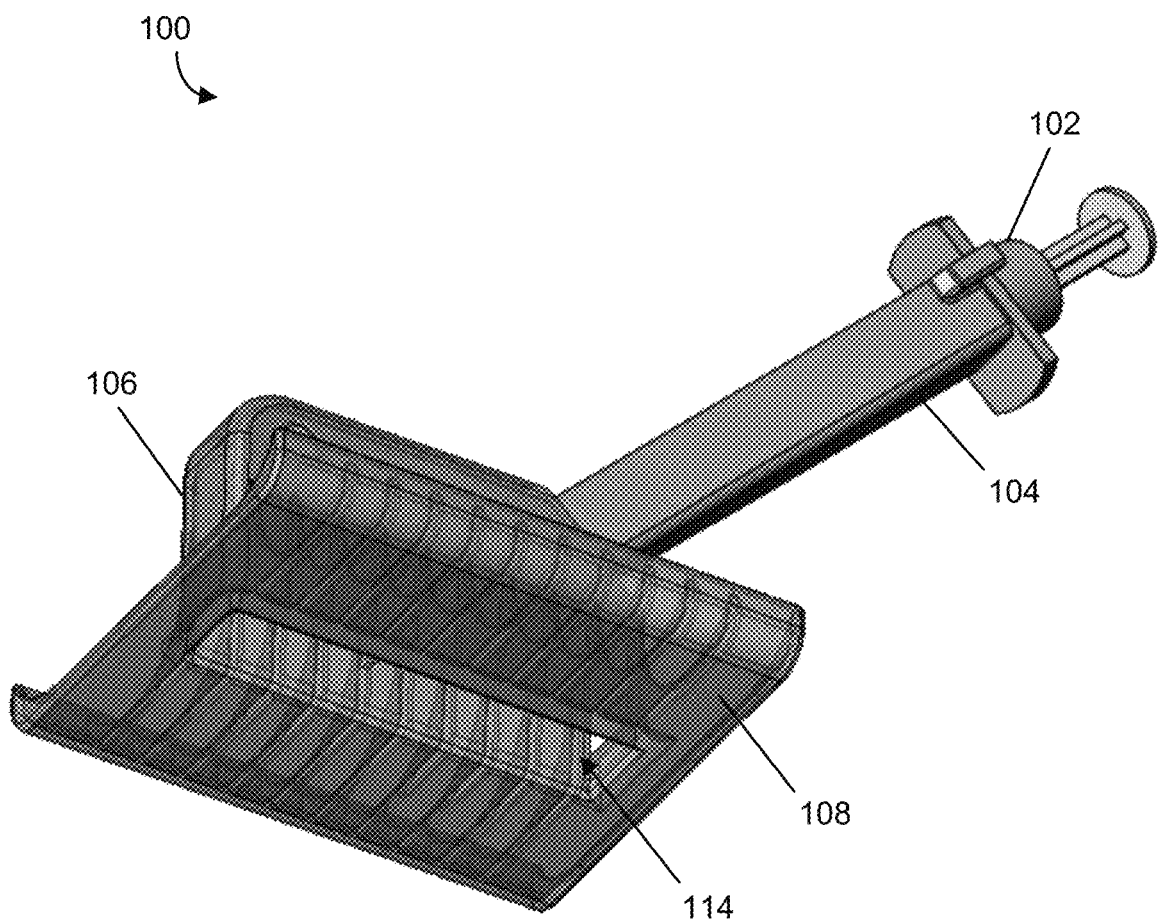
FIG. 2 is another perspective view of the example parenteral injection apparatus of FIG. 1.
Figure 3:
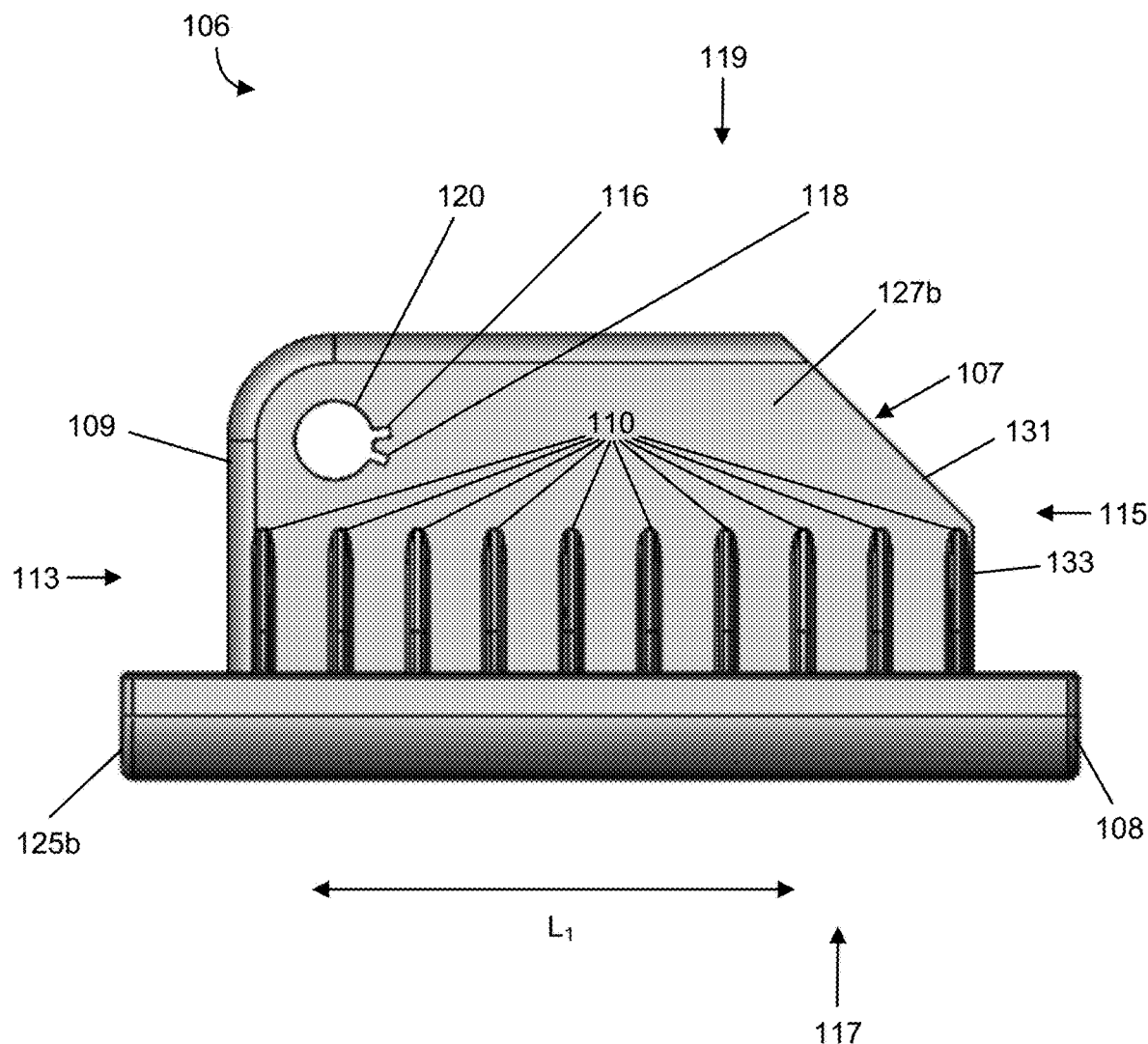
FIG. 3 is a side view of an example injector guide housing.
Figure 4:
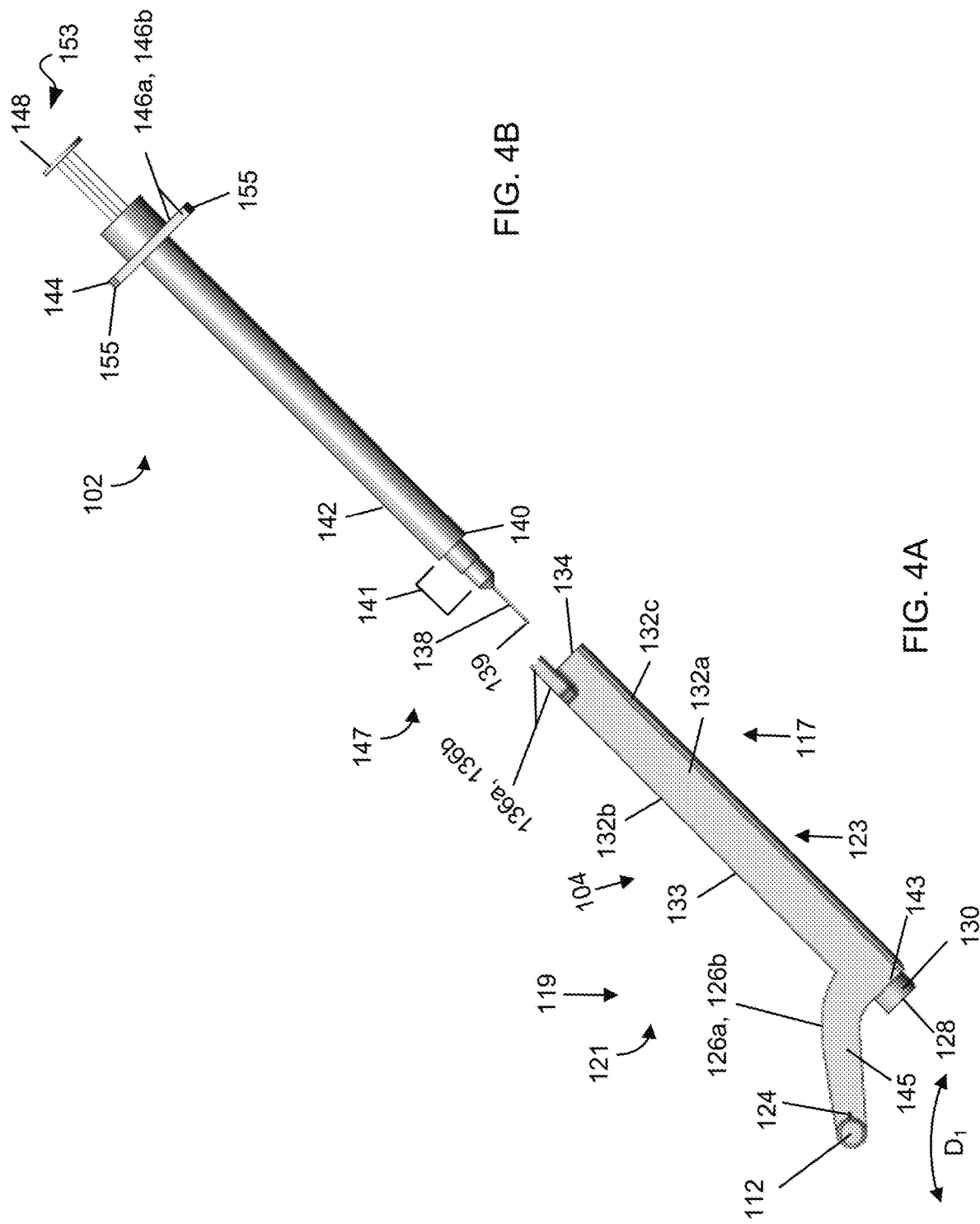
FIG. 4A is a side view of an example injector guide sleeve.
FIG. 4B is a side view of an example injector.

FIG. 1 is a perspective view of an example parenteral injection apparatus 100 (hereinafter "apparatus 100"). FIG. 2 is another perspective view of the example apparatus 100. FIG. 3 is a side view of an injector guide housing 106. FIG. 4A is a side view of an example injector guide sleeve 104. FIG. 4B is a side view of an example injector 102.

In one or more embodiments, the apparatus 100 includes an injector guide sleeve 104 coupled to the injector guide housing 106, in which the housing 106 is configured to receive the injector 102 therein. It is noted that injector 102 may be interchangeably referred to herein, as a syringe. In one or more cases, the sleeve 104 and the housing 106 are configured to be removably and rotatably coupled with one another. For example, the sleeve 104 may rotate about the housing 106 at a pivot point, such as where rotation buttons 112 of the sleeve 104 are coupled to respective rotation hollows 120. In another example, the sleeve 104 and the housing 106 may be packaged separately or disassembled. In such cases, a user may insert the sleeve 104 into an opening 107 of the housing 106, and position the sleeve 104 such that the buttons 112 snap into the respective hollows 120 of the housing. In one or more other cases, the sleeve 104 and the housing 106 are rotatably coupled with one another, and are assembled such that sleeve 104 cannot be removed from the housing 106. The apparatus 100 is defined by a front 113, a rear 115, a top 119, a bottom 117, a right side 121, and a left side 123. Throughout this disclosure, references to orientation (e.g., front, frontward, rear, rearward, in front, behind, above, below, high, low, back, top, bottom, under, underside, right side, left side, etc.) of structural components shall be defined by that component's positioning in FIG. 1 relative to, as applicable, the front 113, the rear 115, the top 119, the bottom 117, the right side 121, and the left side 123 of the apparatus 100, regardless of how the apparatus 100 may be held and regardless of how that component (e.g., the sleeve 104) may be situated on its own (i.e., separated from the housing 106).

In one or more cases, the housing 106 includes a hub 109, contact portion 108, and one or more ribs 110. In one or more cases, the housing 106 may be formed from a rigid material. In some cases, the material may be a transparent or semi-opaque material, which allows a user to see through the housing 106.

The hub 109 may be a rigid plateaued member of the housing 106 that extends upwardly from an upper surface 111 of the contact portion 108 and in a longitudinal direction $L_1$ of the housing 106. The hub 109 includes the opening 107 that faces the rear 115 of the apparatus 100 and is configured to receive the sleeve 106 therein. The opening 107 may be sized to accommodate the rotation of the sleeve 104. When viewed from a side view, such as in FIG. 3, the opening 107 extends from a tapered corner area 131 of the hub 109 to a rear vertical surface 133 of the hub 109. The plateaued member of the hub 109 includes a cavity 114 facing the bottom 117 of the apparatus 100. The cavity 114 of the hub 109 may be sized to allow for the sleeve 104 to rotate within the cavity 114. In one or more cases, the hub 109 may be positioned in a central portion of the housing 106. In one or more other cases, the hub 109 may be offset to the right side 121 or the left side 123 of the housing 106.

The contact portion 108 is a rigid planar member, in which the bottom 117 of the contact portion 108 is configured to contact a surface of a body, e.g., the skin of a human. In one or more cases, the right side 121 and the left side 123 of the contact portion 108 include curved ends 125a, 125b that curve upwards towards the top 119 of the apparatus 100. The bottom 117 of the contact portion 108 may have a smooth surface and curves upwards at the curved ends 125a, 125b. For the cases in which a user presses the housing 106 onto the surface, e.g., skin, of the body, the bottom 117 of the contact portion 108 presses the skin taut, providing a needle 138 of the injector 102 with a flat surface for injection. As such, a user does not need to stretch the skin taut with two fingers in the conventional manner. Moreover, the curved ends 125a, 125b allow the skin to roll around the curved ends 125a, 125b without injuring the skin, as opposed to being pressed against sharp edges if for instance, the contact portion 108 is formed having a substantially planar surface and no curved ends.

In one or more cases, the rib 110 is a reinforcing member that contacts a side wall, e.g., side wall 127b, of the hub 109 and the upper surface 111 of the contact portion 108, and provides structural support for the housing 106, e.g., the hub 109 and the contact portion 108. Additionally, the rib 110 may extend from the upper surface 111 of the contact portion 108 to an upper surface, e.g., upper surface 129b, of a curved end, e.g., curved end 125b, and provides structural support for the housing 106, e.g., the curved ends 125a, 125b of the contact portion 108. In one or more cases, a plurality of ribs 110 may extend across each side, e.g., the right side 121 and the left side 123, of the hub 109 in the longitudinal direction of the hub 109. In one or more other cases, one rib 110 is positioned on each side of the hub 109.

Figure 6A:
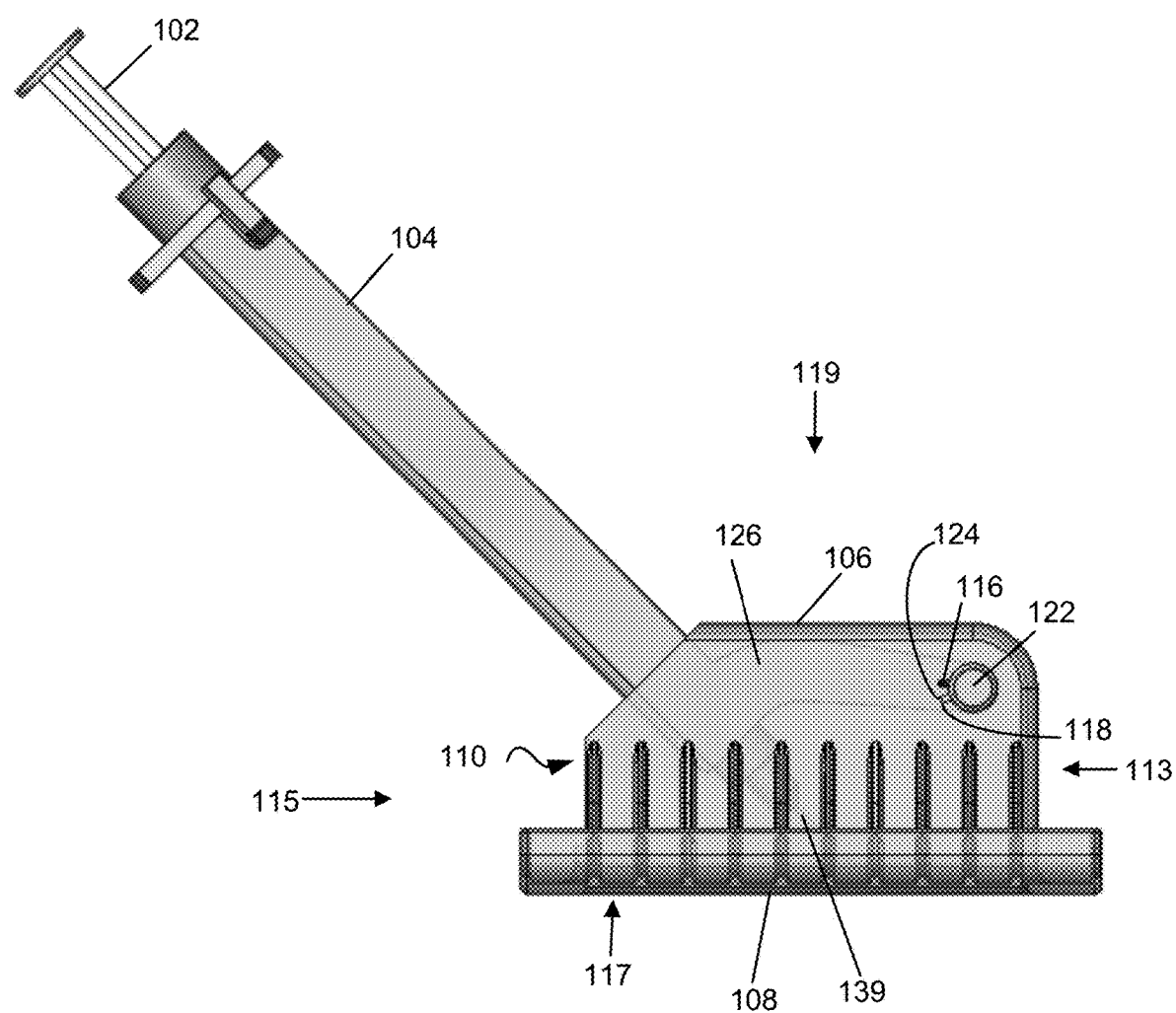
FIG. 6A is a side view of the example parenteral injection apparatus of FIG. 1 in a preparation position.
Figure 6B:
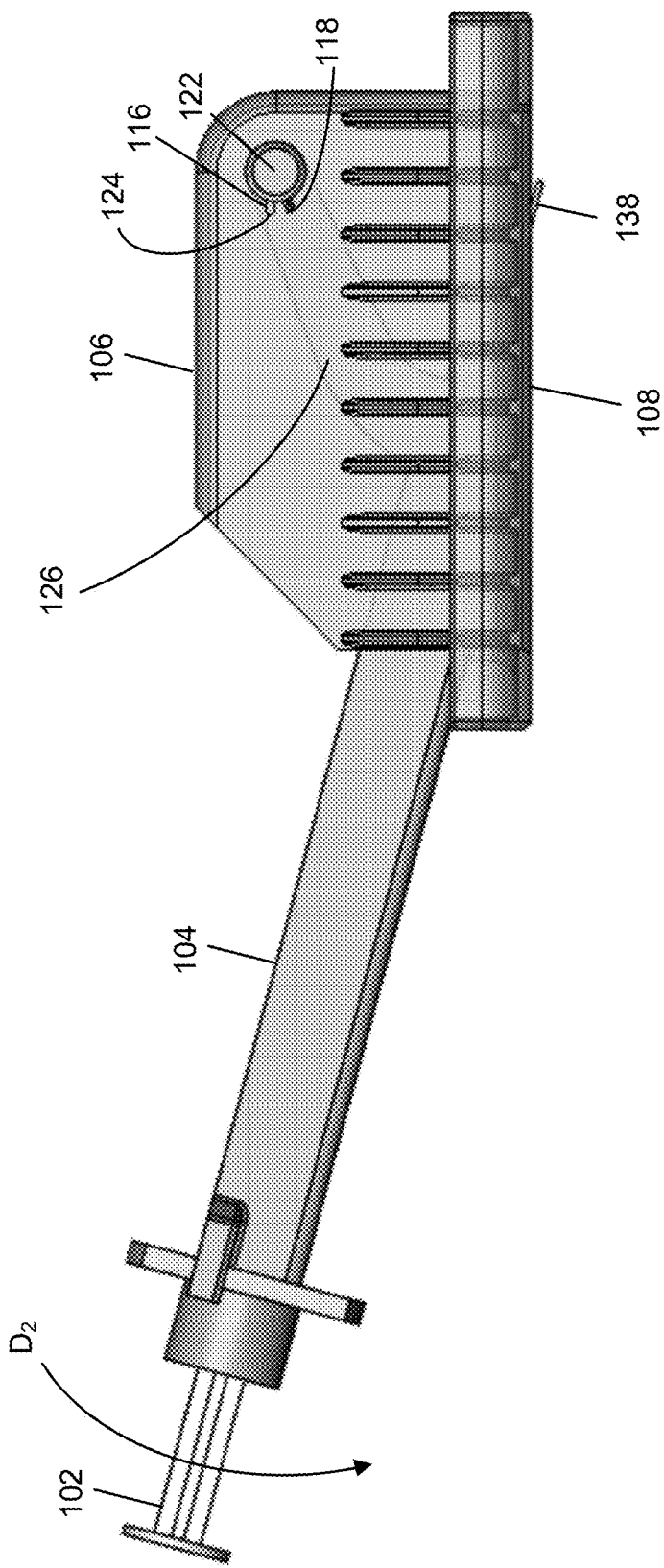
FIG. 6B is side view of the example parenteral injection apparatus of FIG. 1 in an insertion position.

In one or more cases, a side wall, e.g., side wall 127b, of the hub 109 includes a rotation hollow 120. In some cases, both side walls 127a and 127b include a rotation hollow 120. In other cases, only one side wall includes the rotation hollow 120. The rotation hollow 120 may be sized to receive a rotation button 112 of the sleeve 104. For example, the rotation hollow 120 may be a circular hollow within the side wall of the hub 109 and may be configured to receive a cylindrically-shaped button. In one or more cases, the rotation hollow 120 includes one or more rotation recesses, such as rotation recess 116 and rotation recess 118. The rotation recesses 116, 118 are sized to receive a detent 124 of the rotation button 112. In one or more cases, the rotation recess 116, 118 are configured to prevent rotation of the sleeve 104 when the detent 124 is positioned with the rotation recess. A position of a rotation recess along the circumference of the rotation hollow 120 corresponds to a rotation position of the injector 102 and sleeve 104. For example, for the cases in which the detent 124 is positioned within the rotation recess 118, the sleeve 104 is positioned in a preparation position, as shown in FIG. 6A. In another example, for the cases in which the detent 124 is positioned with the rotation recess 116, the sleeve 104 is positioned in an insertion position, as shown in FIG. 6B. In one or more cases, the rotation recess may correspond to an insertion angle of the needle 138 of the injector 102. For example, while the detent 124 is positioned within the rotation recess 116, the needle 138 is positioned at a 15° angle from parallel to the surface of the skin. As such, the rotation recess 116 may be used to perform an intradermal injection.

It is noted that while two rotation recesses are described, additional rotation recesses may be positioned around the rotation hollow 120 to provide additional insertion angles. For example, one rotation recess may be used to position the needle 138 at a 5° angle from parallel to the surface of the skin, and another recess may be used to position the needle 138 at a 45° angle from parallel to the surface of the skin. To allow the detent 124 to rotate into the desired recess, blocking detents of a guide attachment may be inserted within the recesses other than the desired recess, thereby preventing the detent 124 from rotating within a recess other than the desired recess. For example, to insert the needle 138 at a 5° angle into the skin, a user may set the guide attachment such that the blocking detents are inserted into the recesses corresponding to the 15° angle and the 45° angle, thereby allowing the detent 124 to rotate into the recess corresponding to the 5° angle. Accordingly, the apparatus 100 may be used to perform a variety of injections, for example, but not limited to intradermal injections and subcutaneous injections.

Further, it is noted that although apparatus 100 is described as the hub 109 including the rotation hollows 120 and rotation recesses 116, 118, and the sleeve 104 including the rotation button 112 and detent 124, it should be understood that the apparatus 100 may be configured such that the hub 109 includes the rotation button 112 and detent 124 and the sleeve 104 includes the rotation hollows 120 and rotation recesses 116, 118.

In one or more cases, the sleeve 104 may be a rigid channel formed of guide walls 132a, 132b, and 132c disposed between a first end 128 and a second end 134. The guide wall 132a may be positioned on the right side 121 of the sleeve 104, the guide wall 132c may be positioned on a bottom side 117 of the sleeve 104, and the guide wall 132b may be positioned on the left side 123 of the sleeve 104. For example, the guide walls 132a, 132b, 132c may form a "U"-like shape. The top portion 133 of the sleeve 104 may be open allowing the user to view a portion of the injector 102, e.g., a barrel 142 of the injector 102. In one or more other cases, the sleeve 104 may include guide walls or a singular guide wall that encloses the sleeve 104, such that portions of the injector 102 (e.g., the barrel 142) are not physically exposed while in the sleeve 104. In such cases, the sleeve 104 may be formed from a transparent, semi-opaque, or other like material that allows a user to see the injector 102 within the sleeve 104.

The first end 128 of the sleeve 104 includes an aperture 130 that is sized to receive the needle 138 and/or the hub 141 of the injector 102. A proximal end 143 of the aperture 130 may be sized to prevent end 140 of the barrel 142 from extending beyond the proximal end 143 of the aperture 130. In one or more cases, guide arms 126a, 126b are positioned on a portion of the first end 128 of the sleeve 104. A proximal end of the guide arm 126 may be integrally formed with a guide wall 132. For instance, guide arm 126a is integrally formed with guide wall 132a, and guide arm 126b is integrally formed with guide wall 132b. A distal end of the guide arm 126 includes a rotation button 112 and corresponding detent 124. A body 145 of the guide arm 126 may be curved in a direction $D_1$, in which the curve of the body 145 faces the bottom 117 of the apparatus 100. The angle of the curved body 145 may be used in conjunction with the position of a rotation recess of the housing 106 to determine an insertion angle of the needle 138. For instance, the body 145 may be curved at an angle such that the body 145 may be rotated 30° downwards to position the rotation button 112 into the rotation recess 116, thereby providing the needle 138 with a 15° insertion angle into the surface of the skin. In one or more cases, the guide arms 126 may be flexibly rigid members, such that the guide arms 126 may flex towards one another in a lateral direction $L_2$ of the apparatus 100, but rigid enough to support the rotation of the sleeve 104 about the rotation hollows 120. For instance, when the sleeve 104 is assembled with the housing 106, a user may bend the guide arms 126 towards one another, allowing the rotation buttons 112 to fit within the opening 107 of the housing 106. The user may guide the sleeve 104 such that the guide arms 126 spring away from one another fitting the rotation buttons 112 within the respective rotation hollows 120. Although the guide arms 126 are described as two separate members, it should be noted that the guide arms 126 may be a singular rigid member sized to fit within the opening 107 and include one or more spring-actuated push buttons that a user may compress before inserting the guide arm within the opening 107, which decompress outwards and into the rotation hollows 120.

Figure 5:
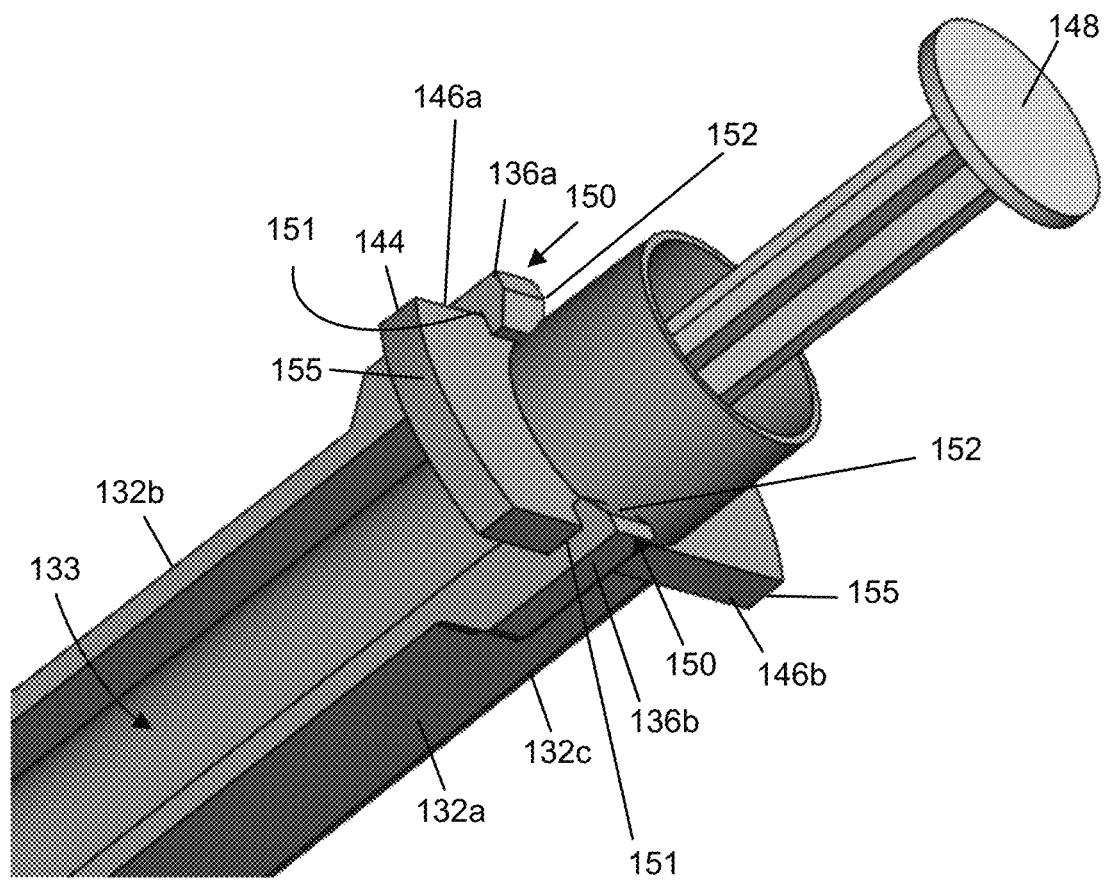
FIG. 5 is an enlarged perspective view of the example injector of FIG. 4B inserted into the example injector guide sleeve of FIG. 4A.

The second end of the sleeve 104 includes an opening to receive the injector 102 and one or more interlocking members 136a, 136b. The interlocking members 136a, 136b may be disposed opposite one another, in which each interlocking member 136a, 136b are formed on guide walls 132a and 132b, respectively. The interlocking members 136a, 136b may be configured to interlock with interlocking members 146a and 146b of the injector 102, as shown in FIG. 5. By interlocking members 136a and 136b with members 146a and 146b, the injector 102 may be secured within the sleeve 104. In one or more cases, the interlocking members 136a, 136b may each include a flexible clip 150 with a tapered end 152. As the injector 102 is inserted into the sleeve 104, the interlocking members 146a and 146b, disposed on the sides of a flange 144 of the injector 102, may contact the tapered ends 152, thereby expanding the flexible clips 150 away from one another. As the injector 102 is further inserted into the sleeve 104, the interlocking members 146a and 146b fit within recesses 151 of the clips 150, such that the flexible clips 150 decompress and lock the interlocking members 146a and 146b with the interlocking members 136a and 136b. To remove the injector 102 from the sleeve 104, a user may bend the clips 150 away from one another, thereby unlocking the injector 102, and may remove the injector 102 from the sleeve 104.

The injector 102 includes the hollow barrel 142 disposed between a plunger end 153 and an insertion end 147. The insertion end 147 may include the hub 141, which is configured to receive the needle 138. In one or more cases, an end 139 of the needle 138 and the gauge size of the needle 138 may correspond to the type of injection being administered. For example, for the cases in which a needle is being injected intradermally, the needle 138 may have a beveled end and may be a 26 or 27-gauge needle. In one or more cases, the length of the needle 138 and the insertion depth of the needle 138 may correspond to the angle of the body 145 and the position of the rotation recess. For example, for the body 145 and the position of the rotation recess to provide a 15° insertion angle into the surface of the skin, the length of the needle 138 may be long enough to penetrate 0.043 inches into the skin. The plunger end 153 may include the plunger 148 and the flange 144 of the barrel 142. The flange 144 includes interlocking members 146a and 146b. The surfaces of the interlocking members 146a and 146b may each include planar surfaces. The planar surfaces of the interlocking members 146a and 146b may be parallel with one another. The flange 144 also includes contact members 155 protruding from the body of the injector 102 and disposed in between the interlocking members 146a and 146b. In some cases, the contact members 155 may be rigid and have planar surfaces or curved surfaces. The contact members 155 may provide a user with an area to grasp with the user's fingers as the plunger 148 is depressed into the barrel 142. In one or more cases, the beveled end 139 of the needle 138 may be aligned with a contact member 155 to provide an indication of an orientation of the beveled end 139. The barrel 142 may be a tubular member configured to house a medicament or another other fluid.

Figure 6C:
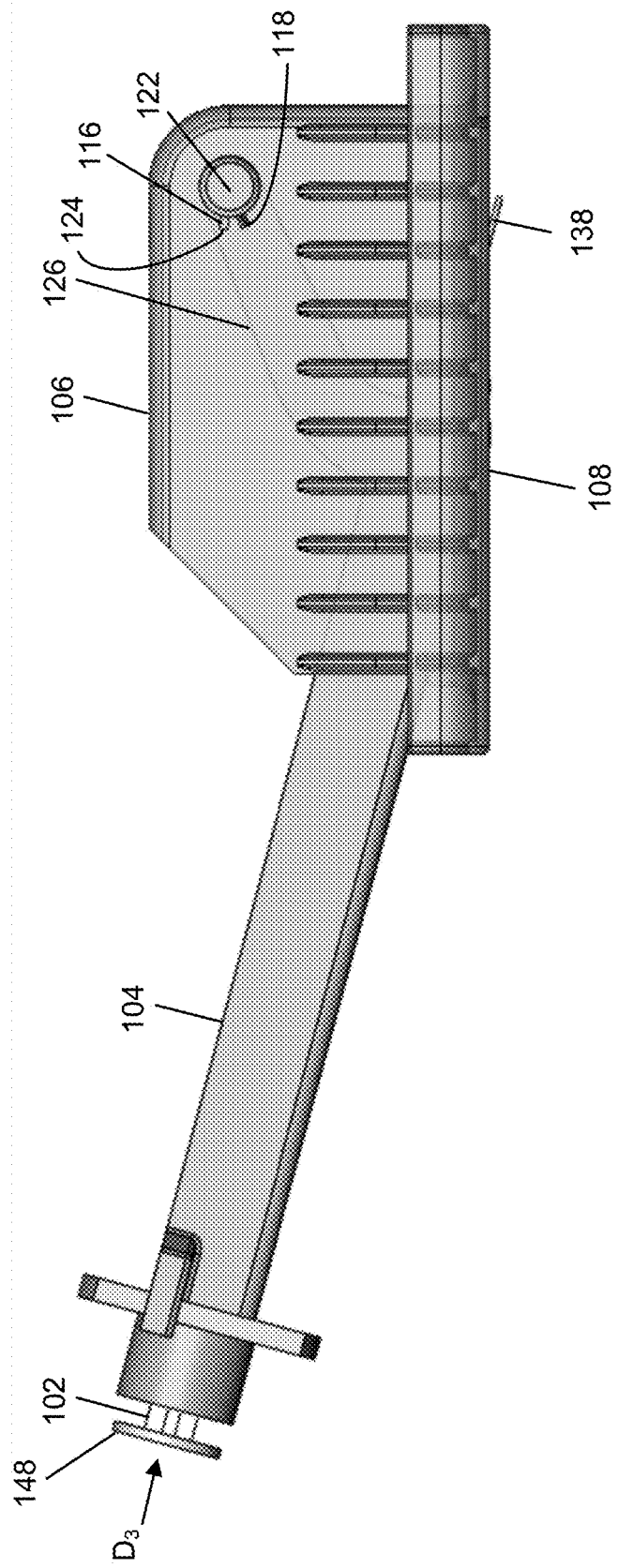
FIG. 6C is a side view of the example parenteral injection apparatus of FIG. 1 in an injection position.

FIG. 6A is a side view of the apparatus 100 in a preparation position. FIG. 6B is side view of the apparatus 100 in an insertion position. FIG. 6C is a side view of the apparatus 100 in an injection position.

In one or more cases, to administer the medicament or fluid to a patient, a user fills the barrel 142 of the injector 102, and subsequently inserts the injector 102 into the sleeve 104 of the apparatus 100. The injector 102 may be inserted into the sleeve 104 until the interlocking members 146a and 146b of the injector 102 interlock with the interlocking members 136a and 136b of the sleeve 104. In one or more cases, before the user inserts the injector 102 into the sleeve 104, the apparatus 100 may be set in the preparation position, as shown in FIG. 6A. That is, the detents 124 of the rotation buttons 112 may be positioned in rotation recesses 118. The user may position the bottom 117 of the contact portion 108 over a target and on the surface of the body, e.g., the skin of a patient. The user may place the user's fingers on the ribs 110 of the housing 106 and press the contact portion 108 on the skin. The user's other hand or a hand of another user depresses the rotation buttons 112 inwards towards each other, allowing the sleeve 104 to rotate in a direction $D_2$ into the insertion position, as shown in FIG. 6B. That is, the detents 124 of the rotation buttons 112 may be positioned in rotation recesses 116. In the insertion position, the needle 138 is inserted into the skin. When the user hears the detents 124 snapping into the rotation recesses 116 and/or visually sees the detents 124 positioned with the rotation recesses 116, the user determines that the needle 138 is inserted into the skin at an angle for the type of administered injection, e.g., but not limited to, an intradermal injection, and at a depth, e.g., 0.043 inches, corresponding to the type of injection. Having confirmed the injection of the needle 138, the user depresses the plunger 148 of the injector 102 in a direction $D_3$, thereby administering the medicament or other fluid into the patient. To remove the needle 138 from the patient, the user may either remove the apparatus 100 entirely from the surface of the skin, or the user may rotate the sleeve 104 back into the preparation position, i.e., by depressing the rotation buttons 112 and positioning the detents 124 into the rotation recesses 118.

Figure 7:
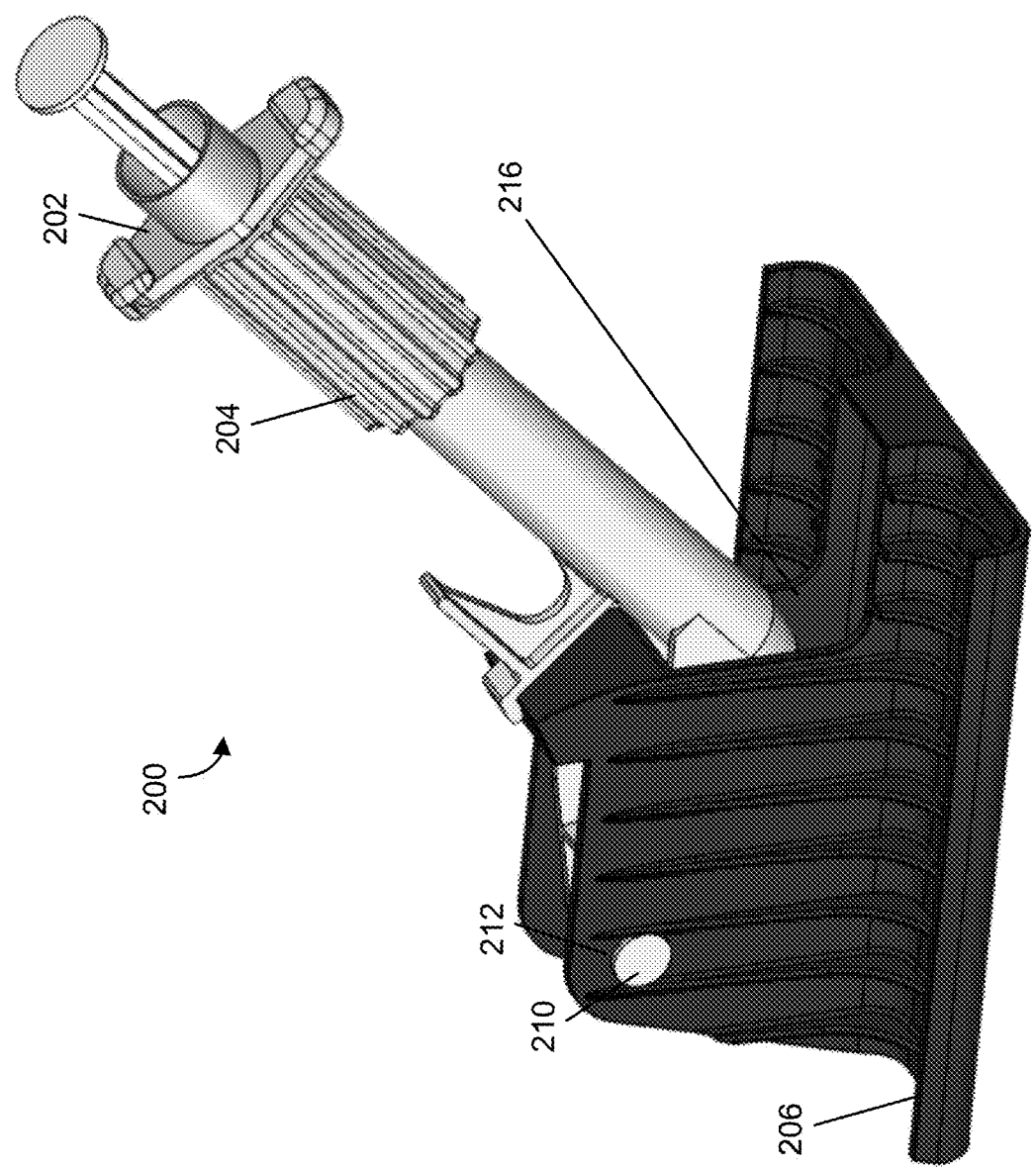
FIG. 7 is a perspective view of another example of a parenteral injection apparatus.

FIG. 7 is a perspective view of another example parenteral injection apparatus 200 (hereinafter "apparatus 200"). The apparatus 200 may include an example injector 202, an injector guide sleeve 204, and a guide housing 206. FIG. 9 is a side view of the injector 202. It should be noted that the injector 202 may be the same as or substantially similar to the injector 102. FIGS. 9A-9H include views of the guide sleeve 204 and components thereof. FIGS. 10A-10D include views of the guide housing 206.

In one or more cases, the apparatus 200 is similar to the apparatus 100 and includes the injector guide sleeve 204 coupled to the injector guide housing 206, in which the housing 206 is configured to receive the injector 202 therein. In one or more cases, the sleeve 204 and the housing 206 are configured to be removably and rotatably coupled with one another. For example, the sleeve 204 may rotate about the housing 206 at a pivot point, such as where rotation buttons 210 of the sleeve 204 are coupled to respective rotation hollows 212 in the housing 206. Consistent with the disclosure of apparatus 100, the sleeve 204 and the housing 206 may be packaged separately or disassembled. In such cases, a user may insert the sleeve 204 into an opening 214 of the housing 206, and position the sleeve 204 such that the buttons 210 snap into the respective hollows 212 of the housing 206. As a result, the sleeve 204 and the housing 206 are rotatably coupled with one another between a plurality of positions.

Figure 8:
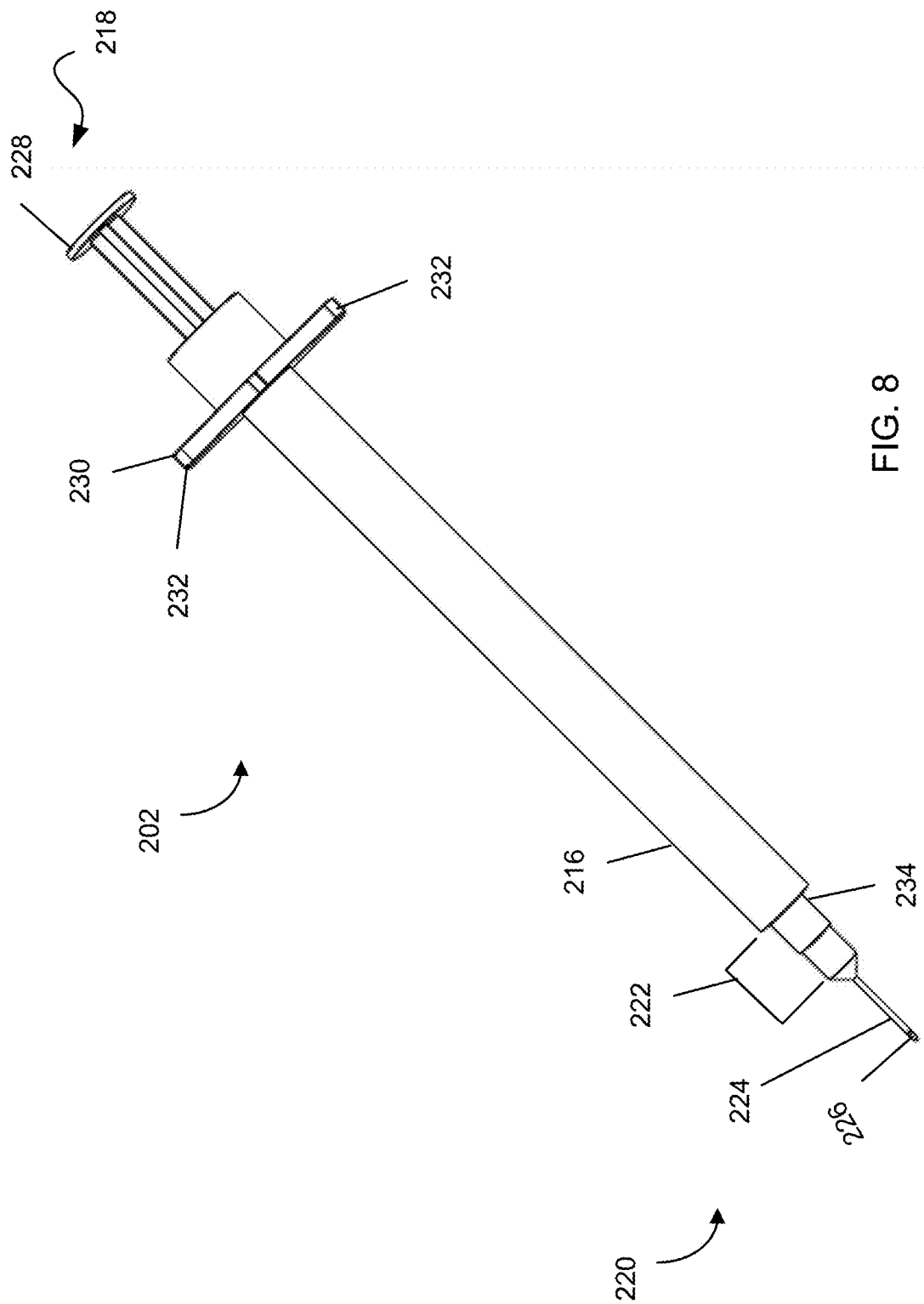
FIG. 8 is a side view of an example injector.

FIG. 8 further illustrates the injector 202. According to an exemplary embodiment, the injector 202 includes a hollow barrel 216 disposed between a plunger end 218 and an insertion end 220. The insertion end 220 may include, for example, a hub 222, which is configured to receive a needle 224. The hub 222 may include a smaller diameter than the barrel 216. In one or more cases, an end 226 of the needle 224 and the gauge size of the needle 224 may correspond to the type of injection being administered. For example, for the cases in which a needle is being injected intradermally, the needle 224 may have a beveled end and may be a 26 or 27-gauge needle. As described with respect to apparatus 100, the needle 224 may be selected based on the positioning provided by the sleeve 204 and the housing 206.

The plunger end 218 of the injector 202 may include a plunger 228 and a flange 230 of the barrel 216. The flange 230 also includes contact members 232 protruding from the body of the injector 202 and disposed in between the interlocking members 230a and 230b. In some cases, the contact members 232 may be rigid and have planar surfaces or curved surfaces. The contact members 232 may provide a user with an area to grasp with the user's fingers as the plunger 228 is depressed into the barrel 216. In some cases, the flange 230 and/or the contact members 232 may facilitate a connection of the injector 202 to the sleeve 204. In some cases, the beveled end 226 of the needle 224 may be aligned with a contact member 232 to provide an indication of an orientation of the beveled end 226. The barrel 216 may be a tubular member configured to house a medicament or another other fluid. The barrel 216 may connect to the hub 222 at an end 234 of the barrel 216. The end 234 may act as a stop for the barrel 216 when it is inserted into the sleeve 204.

Figure 9A:
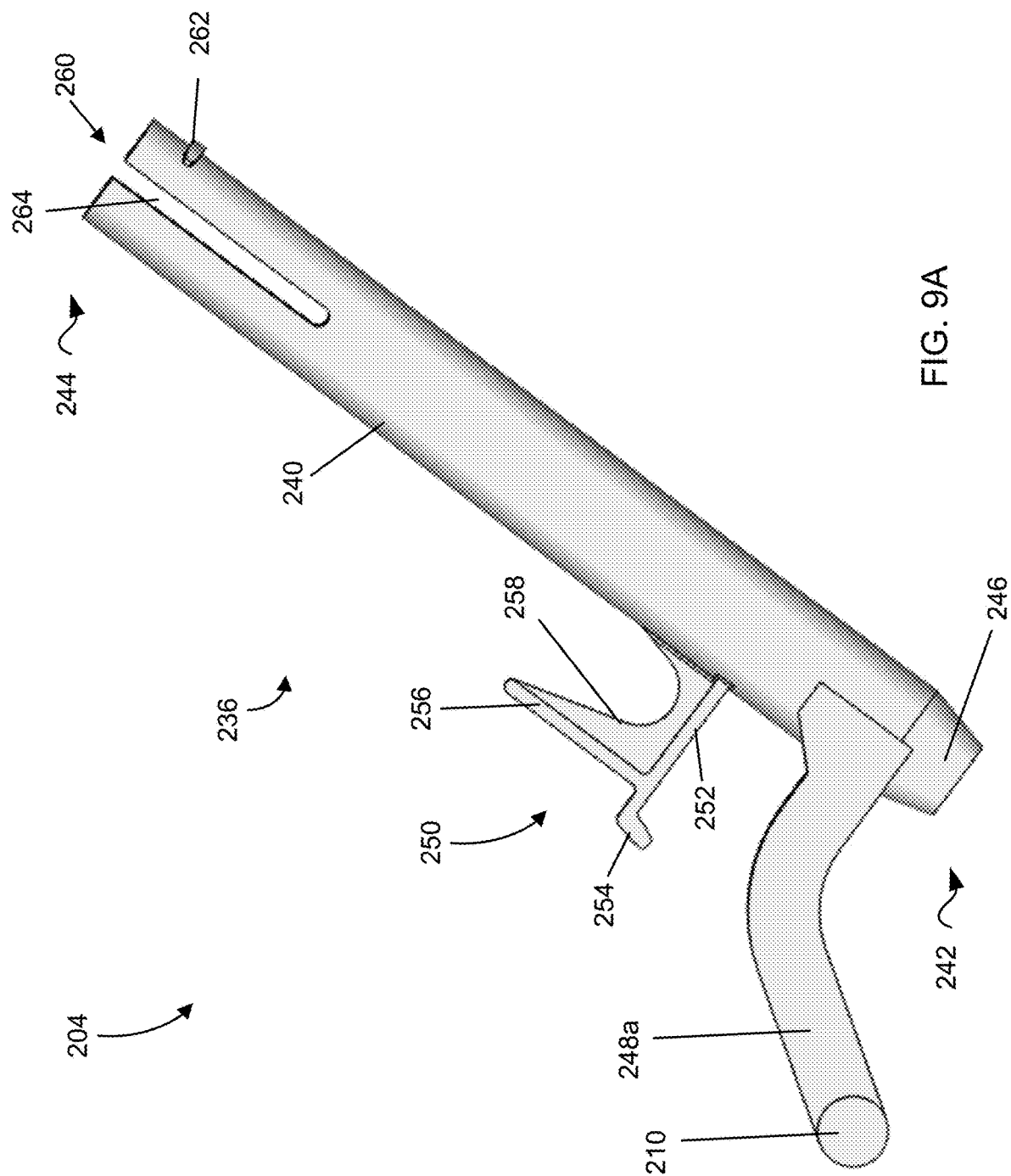
FIG. 9A is a side view of a receiving portion of an example sleeve of the parenteral injection apparatus of FIG. 7.
Figure 9C:
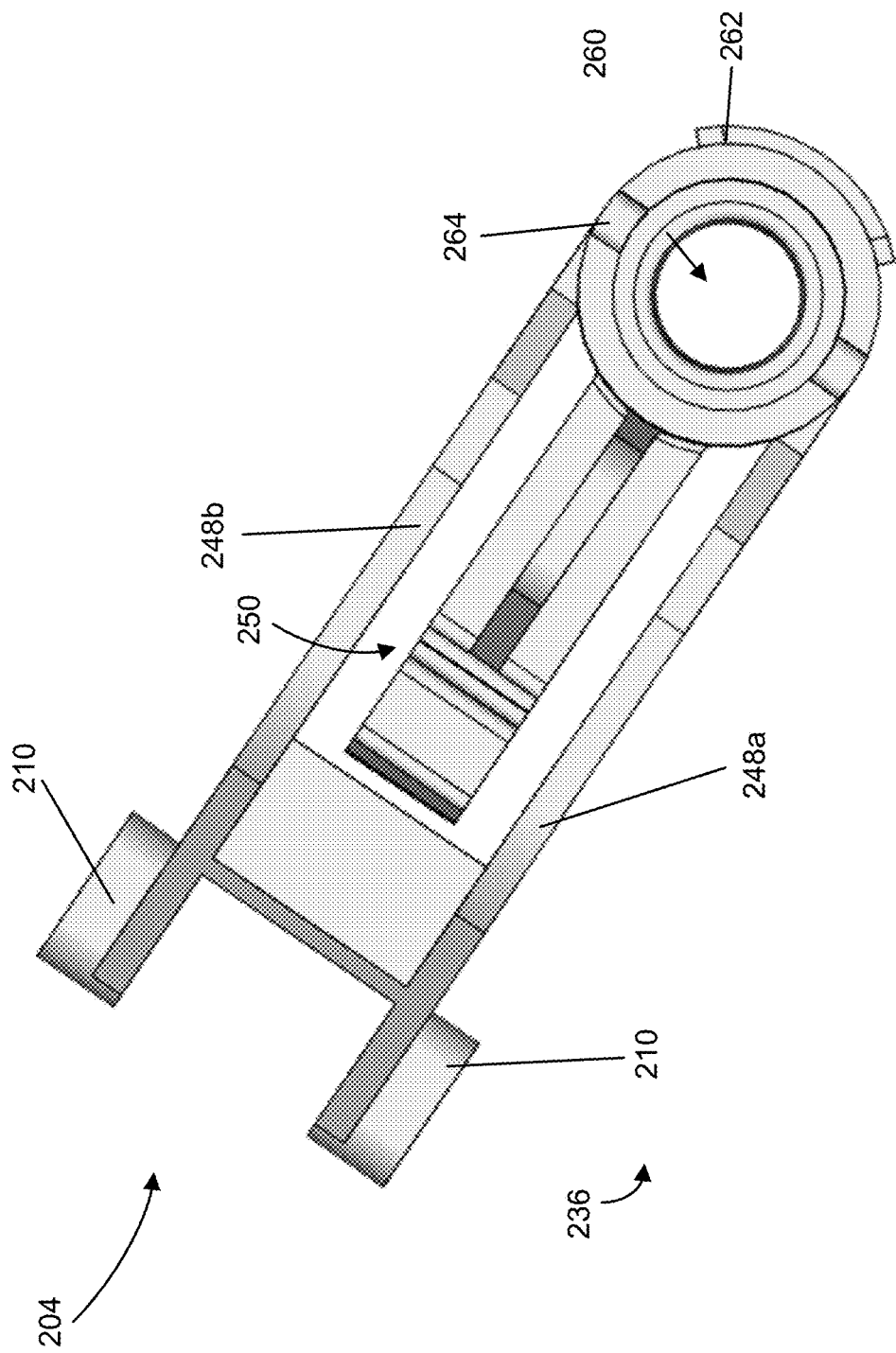
FIG. 9C is a top view of the receiving portion.
Figure 9E:
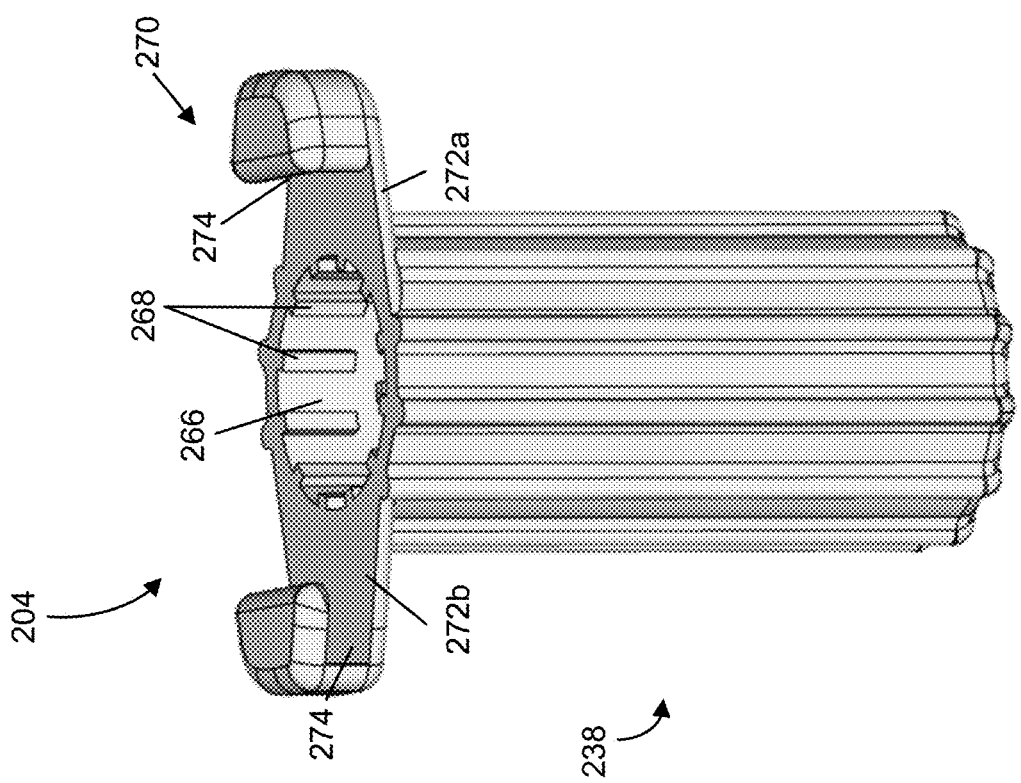
FIG. 9E is a second side view of the connection portion.
Figure 9D:
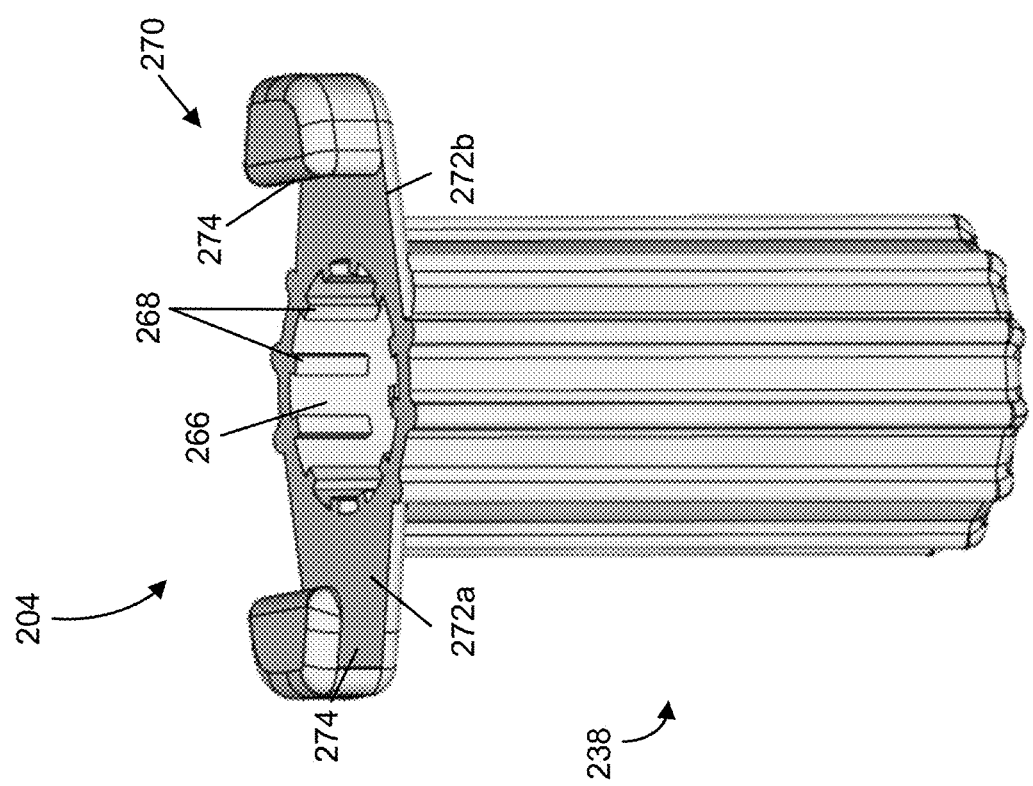
FIG. 9D is a first side view of a connection portion of the sleeve that may be used in conjunction with the receiving portion.
Figure 9F:
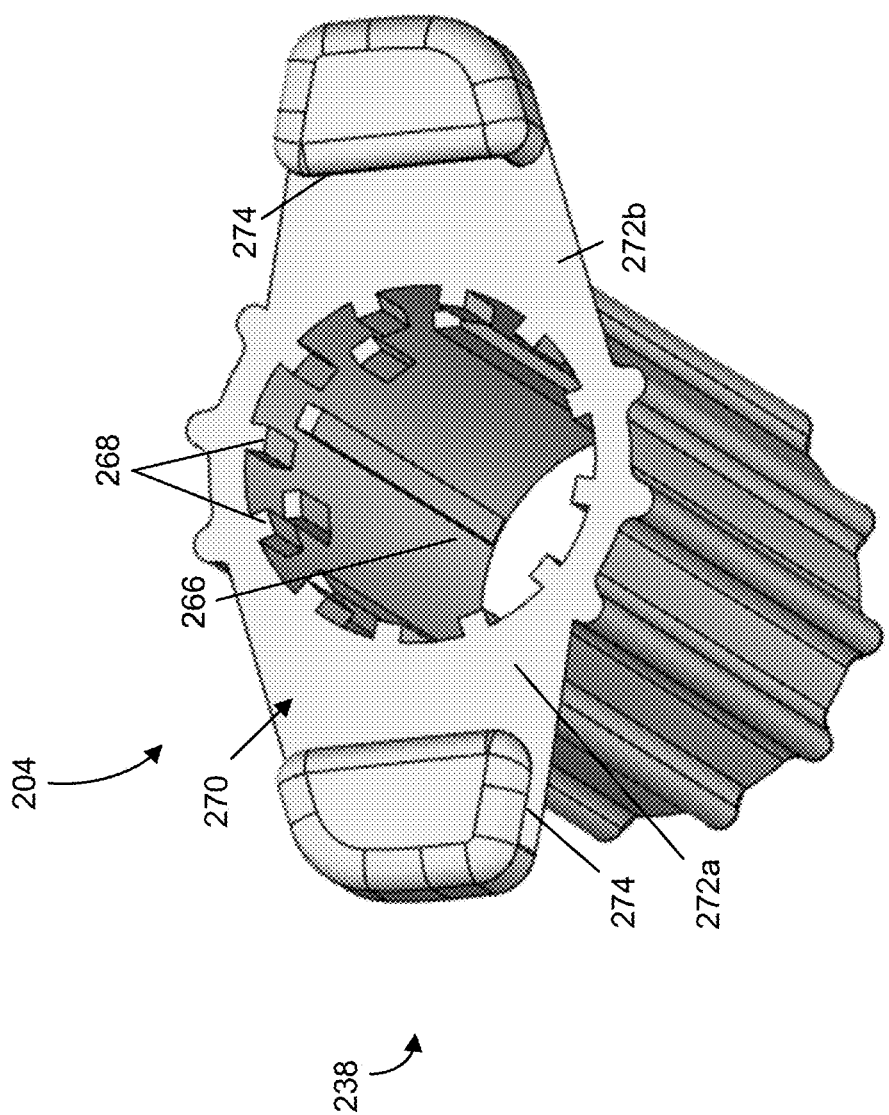
FIG. 9F is a perspective view of the connection portion.
Figure 9G:
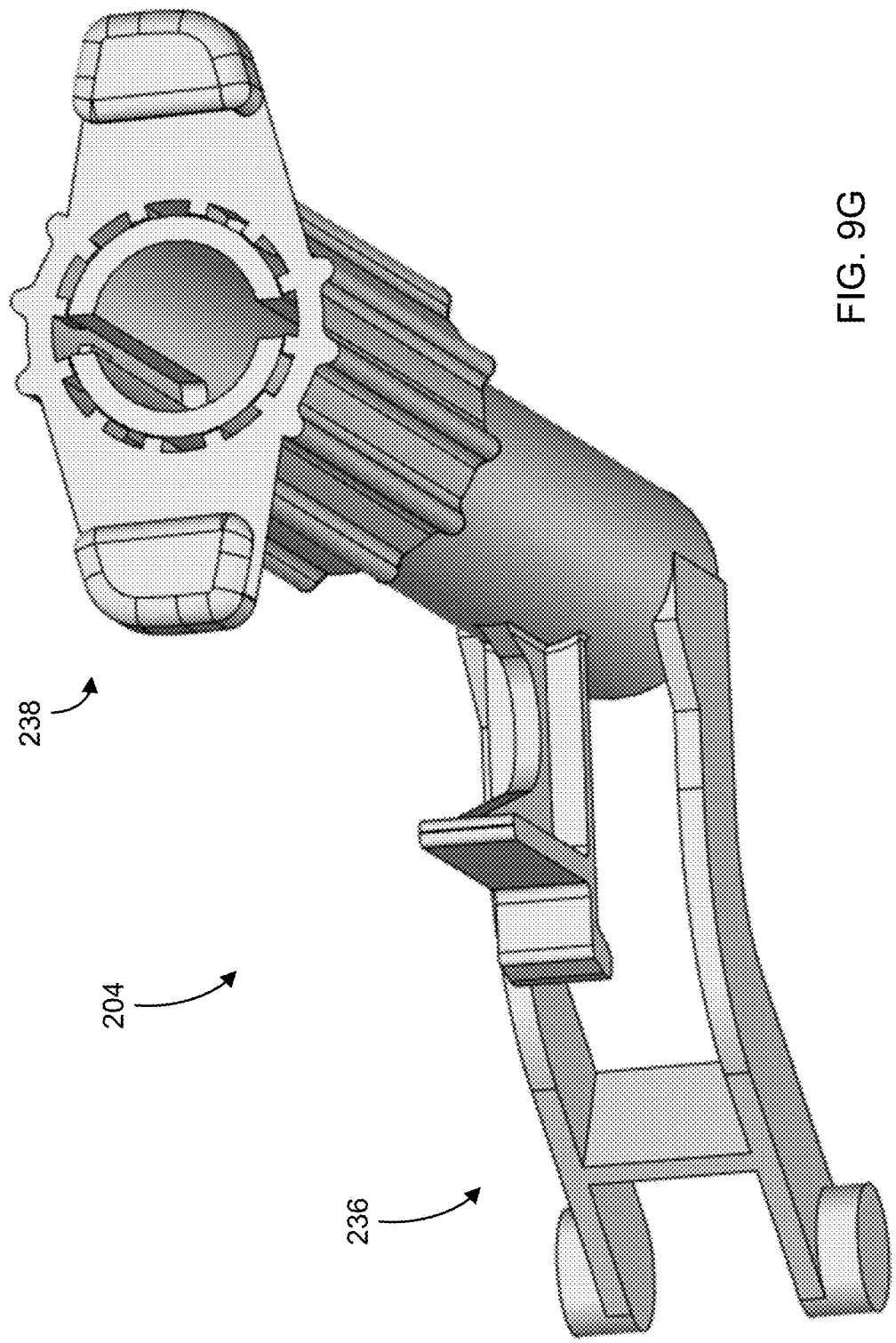
FIG. 9G is a perspective view of the sleeve, including the receiving portion and the connection portion.

FIGS. 9A-9H illustrate an example of the sleeve 204. The sleeve 204 may be similar to the sleeve 104 with some additional and/or alternative features for performing the disclosed functions. The description of the sleeve 104 may apply to the sleeve 204 for at least some features. For example, in some cases, the sleeve 204 may be formed from a transparent, semi-opaque, or other like material that allows a user to see the injector 202 within the sleeve 204. The sleeve 204 may include a receiving portion 236 (FIGS. 9A-9C) and a connection portion 238 (FIGS. 9D-9F). The connection portion 238 may be configured to attach to the receiving portion 236. The receiving portion 236 may include a rigid channel 240 disposed between a first end 242 and a second end 244 and configured to receive the barrel 214 of the injector 202 and attach to the connection portion 238. The connection portion 238 may be configured to connect to the flange 230 of the injector 202.

The first end 242 of the sleeve 204 includes an aperture 246 that is sized to receive the needle 224 and/or the hub 222 of the injector 202. A proximal end of the aperture 246 may be sized to prevent end 234 of the barrel 216 from extending beyond the proximal end of the aperture 246. The receiving portion 236 may further include guide arms 248a, 248b positioned on a portion of the first end 242 of the channel 240. A proximal end of each guide arm 248a, 248b may be attached to and/or integrally formed with an outer surface of the channel 240. A distal end of each guide arm 248a, 248b includes the rotation button 210.

Each guide arm 248a, 248b may be curved downwardly as they extend away from the channel 240. A trajectory and angle of the curved guide arms 248a, 248b may be selected in conjunction with a position of a rotation hollows 212 of the housing 206 to determine an insertion angle of the needle 224. For instance, the body guide arms 248a, 248b may be curved at an angle to provide the needle 224 with a 15° insertion angle into the surface of the skin. In one or more cases, the guide arms 248a, 248b may be flexibly rigid members, such that the guide arms 248a, 248b may flex towards one another, but rigid enough to support the rotation of the sleeve 204 about the rotation hollows 212 of the housing 206. For instance, when the sleeve 204 is assembled with the housing 206, a user may bend the guide arms 248a, 248b towards one another, allowing the rotation buttons 210 to fit within the opening 214 of the housing 106. The user may guide the sleeve 204 such that the guide arms 248a, 248b spring away from one another fitting the rotation buttons 210 within the respective rotation hollows 212. Although the guide arms 248a, 248b are described as two separate members, it should be noted that the guide arms 248a, 248b may be a singular rigid member sized to fit within the opening 214 and include one or more spring-actuated push buttons that a user may compress before inserting the guide arm within the opening 214, which decompress outwards and into the rotation hollows 212.

In one or more cases, the receiving portion 236 further includes a positioning member 250. The positioning member 250 may be configured to interface and interact with the housing 206 to assist in holding the sleeve 204 and injector 202 in a selected position of a plurality of positions made possible by the rotatable connection between the sleeve 204 and the housing 206. The positioning member 250 may project from the outer surface of the channel 240. The positioning member 250 may include an extension 252, a hook portion 254, and a contact portion 256. The extension 252 may extend away from the channel 240 and be configured to flex to a degree to control and move the hook portion 254. The contact portion 256 may extend generally perpendicularly to the extension 252 and provide a grasping portion for a user's finger to cause flexing of the extension 252 to thereby control the hook portion 254 and assist in movement of the sleeve 204 with respect to the housing 206. A reinforcing member 258 may be connected between the extension 252 and contact portion 256 to provide a safeguard against breakage of the extension 252 during flexing. While the hook portion 254 is nominally called a "hook" it does not necessarily include a hook-shape (e.g., it does not need to be curved like a hook to provide a locking/latching function described herein.)

The second end 244 of the receiving portion 236 includes an opening 260 to receive the injector 202 and is configured to attach (removably or permanently) to the connection portion 238. The receiving portion may include connection features, such as a protrusion 262 and/or one or more slots 264 to assist in attaching the receiving portion 236 to the connection portion 238.

FIGS. 9D-9F further illustrate an example connection portion 238. FIG. 9D is first side view and FIG. 9E is an opposite second side view, showing a symmetry of the connection portion 238 as the views appear the same. The connection portion 238 may include a bore 266 configured to receive a portion of the second end 244 of the receiving portion 236 of the sleeve 204. An interior surface of the bore 266 may include one or more mating projections 268 configured to interact with the connection features of the receiving portion 236 to attach the connection portion 238 to the receiving portion 236.

Figure 9H:
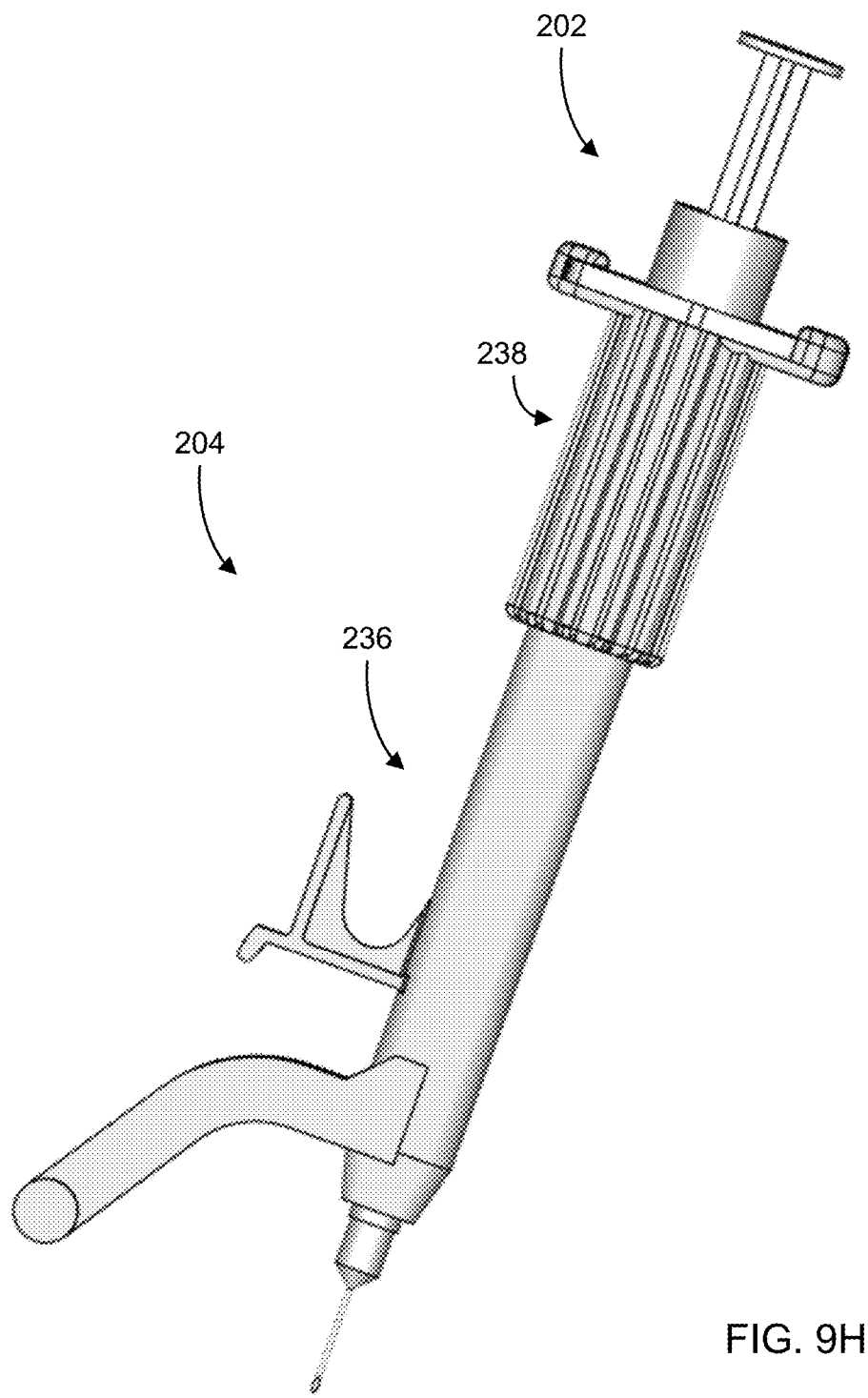
FIG. 9H is a siew view of the injector inserted into the sleeve.

The connection portion 238 may further include a flange 270 including a first portion 270a and a second portion 270b extending in opposite directions and generally corresponding to a shape of the flange 230 of the injector 202. Each portion 270a, 270b of the flange 270 may include a receiving slot 274 for receiving a respective contact member 232 of the flange 230 of the injector 202, thereby connecting the injector 202 to the sleeve 204. The receiving slots 274 may be open only on one side, with the openings of the receiving slots 274 being opposite from each other, such that a twisting or rotational motion of the injector 202 in the sleeve 204 will cause the contact portions 232 to enter into the receiving slots 274 and thereby firmly connect the injector 202 to the sleeve 204, as shown in FIG. 9H. In some embodiments, the connection portion 238 may be attached the injector 202 and then the combined assembly inserted into the receiving portion 236.

FIGS. 10A-10D further illustrate the housing 206. In one or more cases, the housing 206 includes a hub 276, contact portion 278, and one or more ribs 280 providing reinforcement between the hub 276 and the contact portion 278. In one or more cases, the housing 206 may be formed from a rigid material. In some cases, the material may be a transparent or semi-opaque material, which allows a user to see through the housing 206.

Figure 10A:
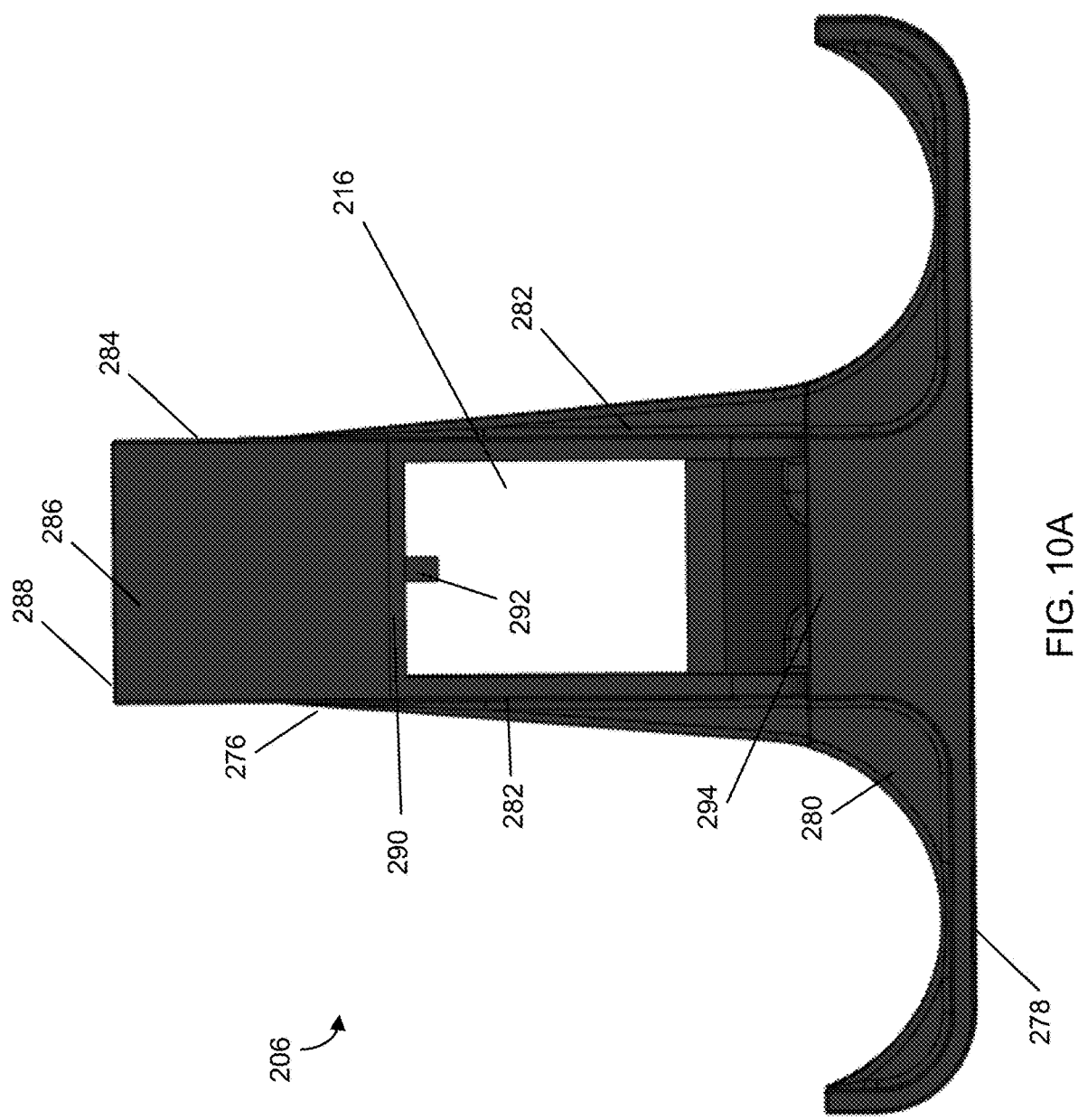
FIG. 10A is a front view of an example injector guide housing of the parenteral injection apparatus of FIG. 7.
Figure 10B:
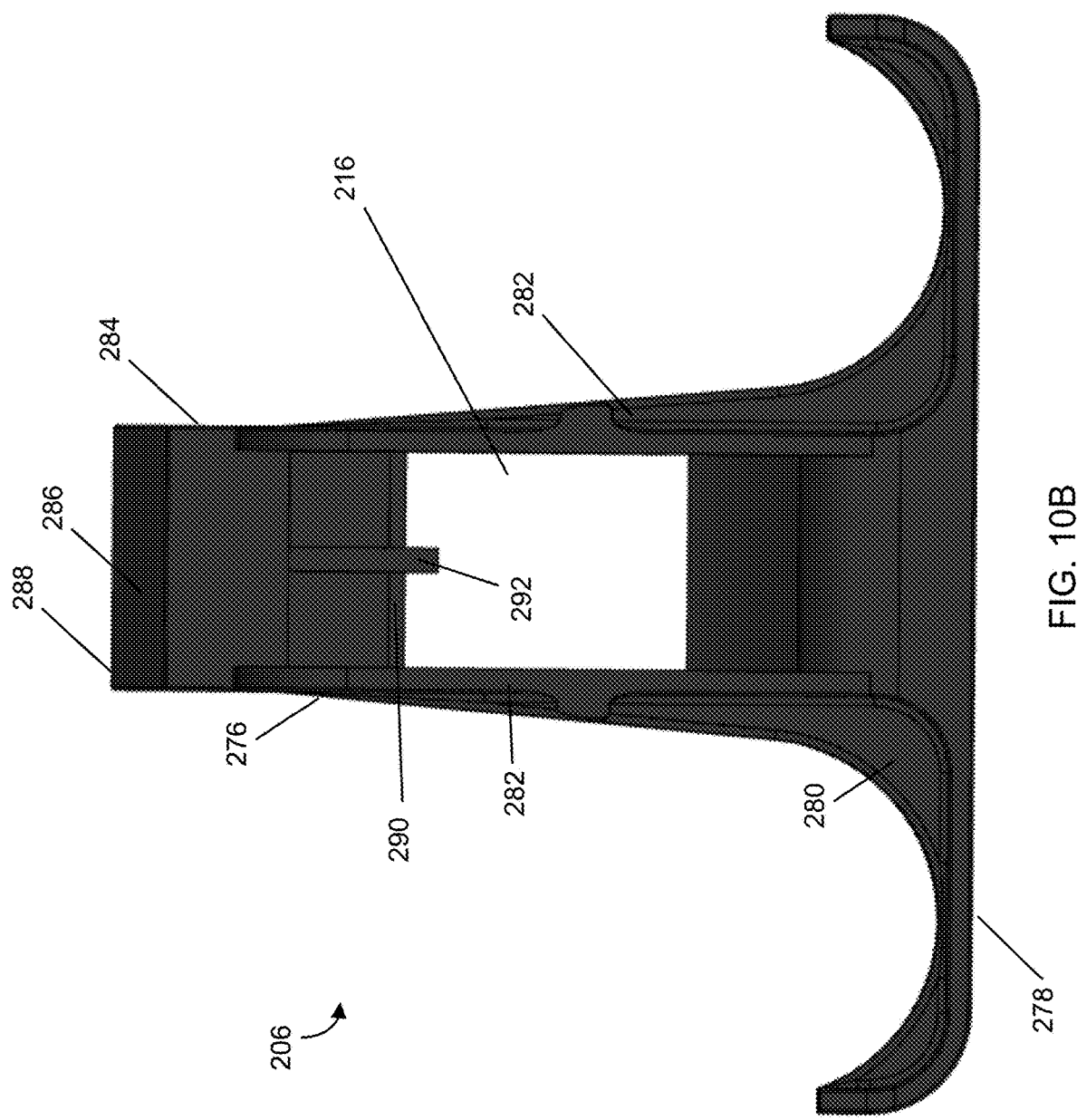
FIG. 10B is a rear view of the guide housing.
Figure 10C:
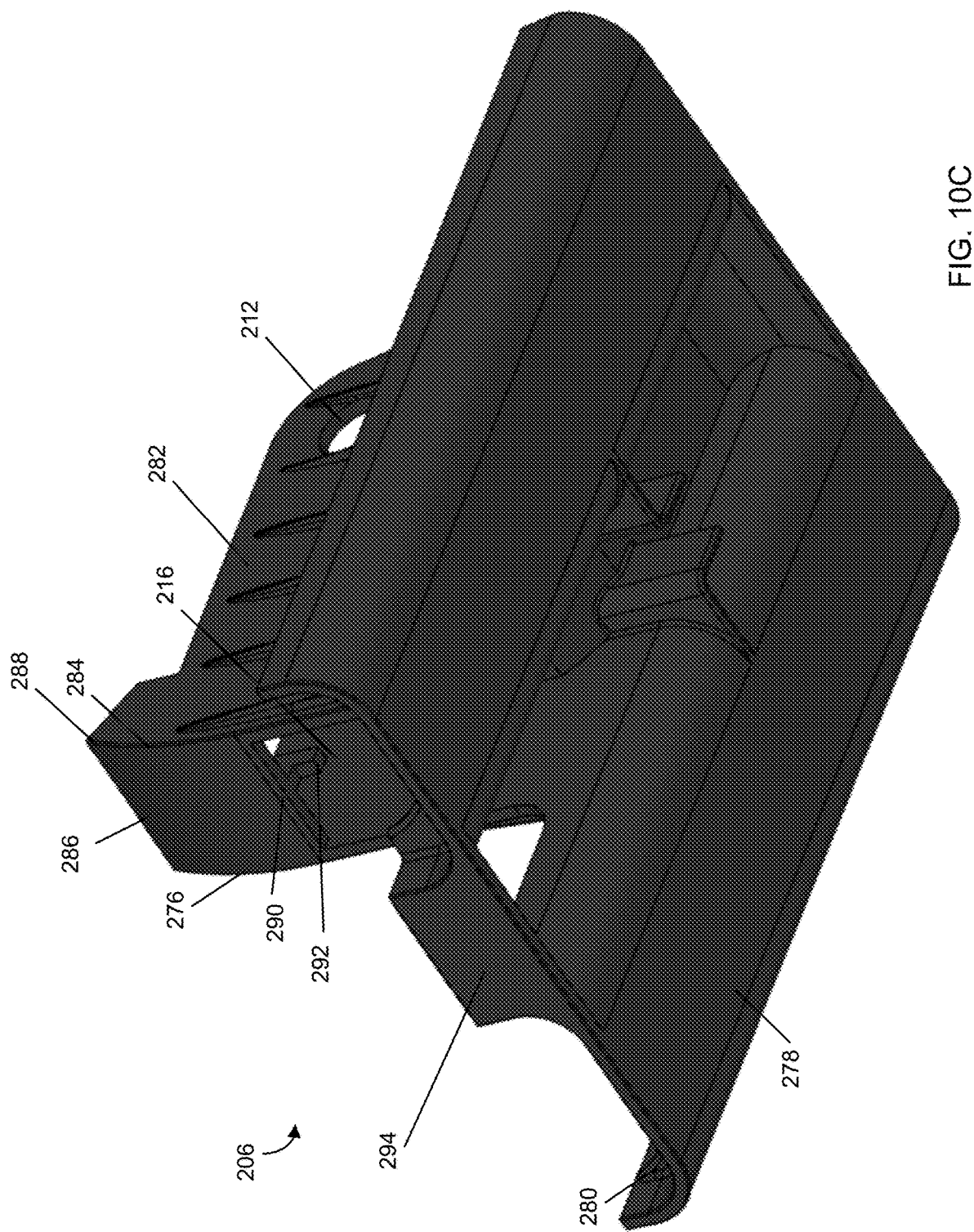
FIG. 10C is a perspective view of the guide housing.
Figure 10D:
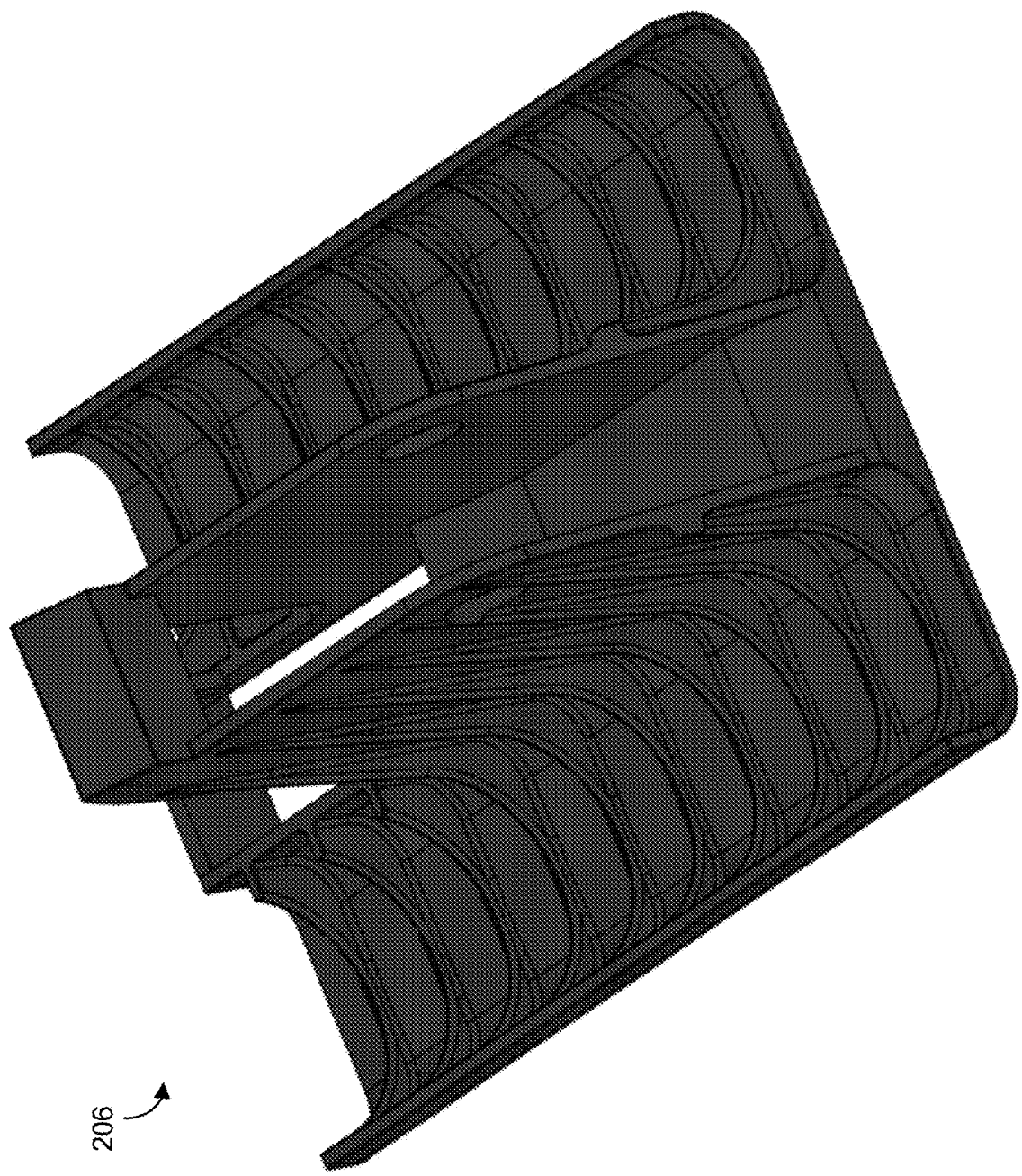
FIG. 10D is another perspective view of the guide housing.

The hub 276 may include a pair of rigid walls 282 extending upwardly from the contact portion 278 and defining the opening 214 for receiving a portion of the sleeve 204 therein. Each wall 282 may include a respective one of the rotation hollows 212. In one or more cases, the hub 276 may be closed on a back-end (similar to the hub 109) or may remain open as shown in FIGS. 7 and 10A-10D. The rigid walls 282 may be connected by a bridge 284 defining an upper limit of the opening 214. The bridge 284 may be configured as a connector for the positioning member 250 to assist in placement of the sleeve 204 in a selected positon. The bridge 284 may comprise a face 286, a top edge 288, a bottom edge 290, and a stop 292 at the bottom edge 290. The face 286 may be generally sloped in a rotational direction of the sleeve 204. The housing 206 may further include a support 294 positioned at a front of the housing 206 at an entrance to the opening 214. The contact portion 278 and the one or more ribs 280 may be configured to perform and function similarly to the corresponding portions shown and described in relation to the housing 106. The contact portion 278 may be placed on a user's skin to facilitate an injection via the injector 202. The ribs 280 may provide reinforcements that help to prevent unwanted deviation from a desired position of the injector 202. Further, in one or more cases, a pair of safety ribs 296 may be formed on or adjacent to the contact portion 278, as seen in FIG. 10C. The safety ribs 296 may provide a guide channel for the injector 202 to help protect against a user accidentally contacting the needle 224 of the injector 202, such as when the injector 202 is inserted into the housing 206 but the contact portion 278 is not yet in place on a patient's skin.

Figure 11A:
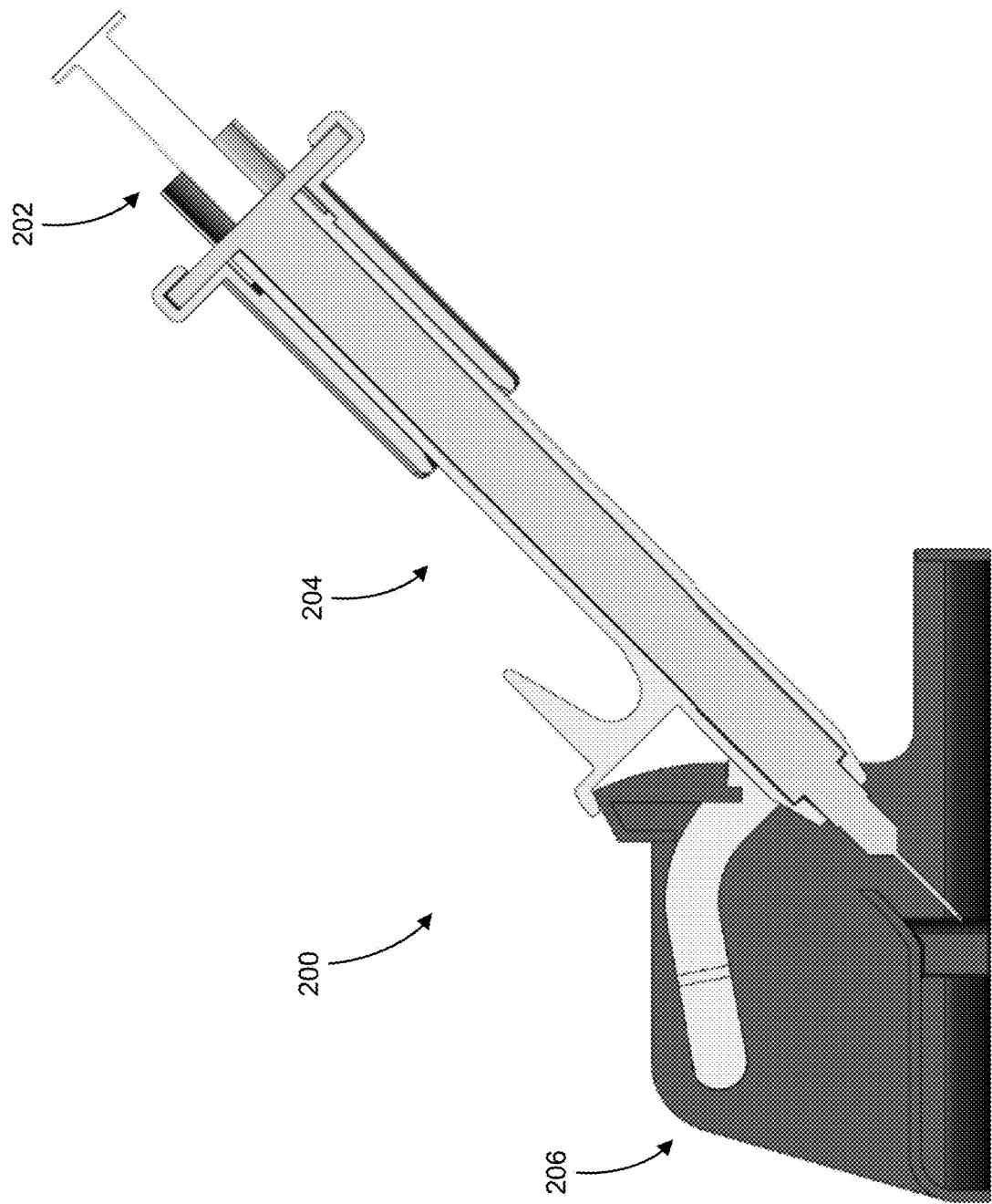
FIG. 11A is a side view of the example parenteral injection apparatus of FIG. 7 in a preparation position.
Figure 11B:
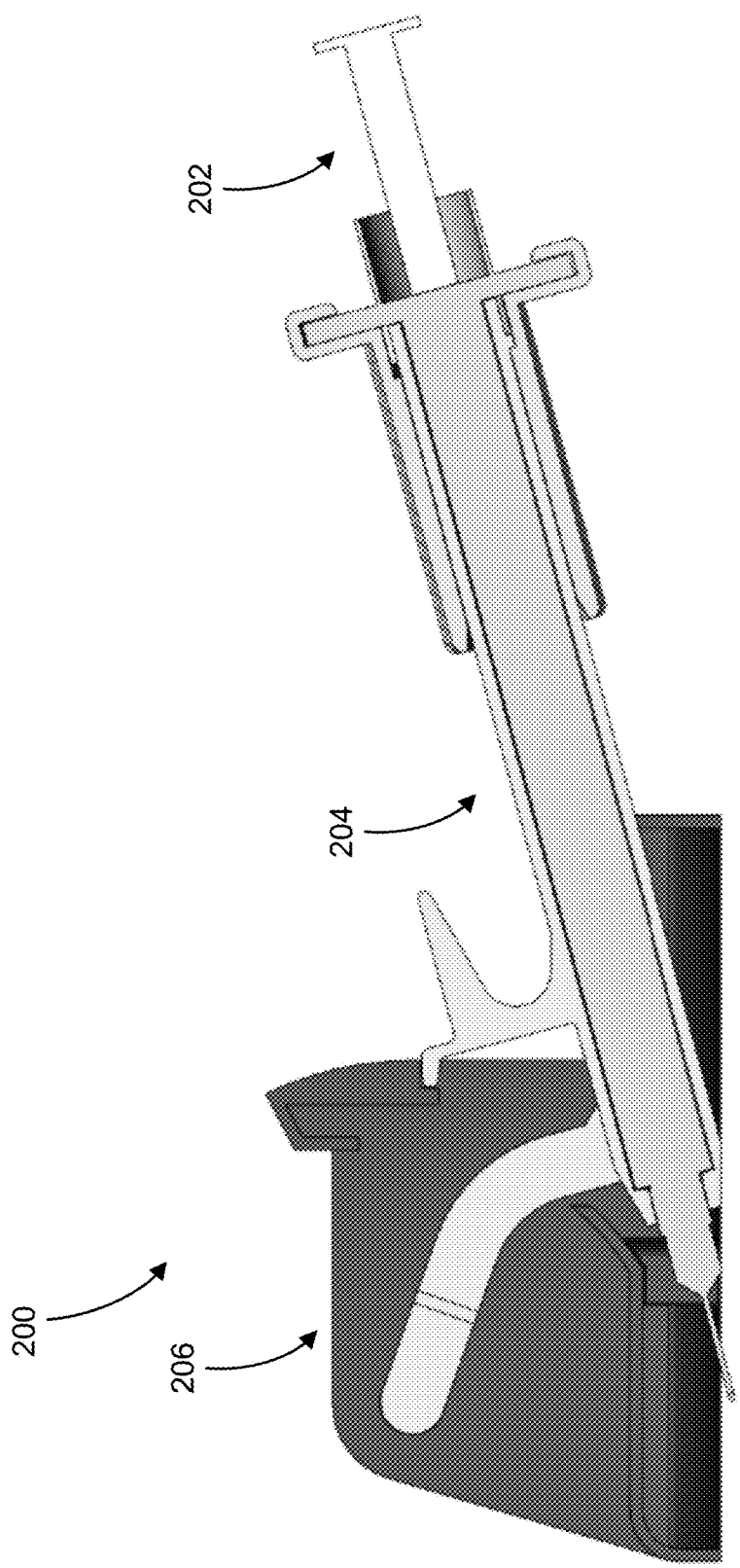
FIG. 11B is side view of the example parenteral injection apparatus of FIG. 7 in an insertion position.

The buttons 210 are configured to be inserted into the rotation hollows 212 to thereby attach the sleeve 204 to the housing 206 and further allow rotational motion between a preparation position, as shown in FIG. 11A, and an insertion position, as shown in FIG. 11B. In at least some embodiments, the positioning member 250 is configured to provide a locking feature to hold the sleeve 204 in either the preparation position or the insertion position, such as by interacting with the bridge 284.

As shown in FIG. 11A, the preparation position may include the hook portion 254 latched onto the top edge 288 of the bridge 284. The extension 252 may be sized such the hook portion engages the top edge 288, thereby inhibiting rotational motion in at least one direction of the sleeve 204. A user may manipulate the contact portion 256 to flex the extension 252 to enable the hook portion 254 to rest on the top edge 288 and thereby hold the sleeve 206 in the preparation position.

As shown in FIG. 11B, the sleeve 206 may be moved to an insertion position to perform an injection on a patient. For example, the needle 224 may be positioned at a 15° angle from parallel to the surface of the skin. The positioning member 250 may lock the sleeve 204 and injector 202 in the insertion position by interacting with the bottom edge 290 and stop 292 of the bridge 284. A user may manipulate the contact portion 256 to flex the extension 252 and enable the hook portion 254 to clear the top edge 288 and allow the sleeve 204 to be rotated downwardly toward the support 294 until the sleeve 206 contacts the support 294. The positioning member 250 may be released such that the hook portion 254 fits under the bottom edge 290 and rests against the stop 292, thereby placing and holding the sleeve 204 in the insertion position. A subsequent injection may be carried out as described herein with respect to the apparatus 100.

It is noted that one or more features of apparatus 100 may integrated with apparatus 200 and one or more of the features of apparatus 200 may be integrated with apparatus 100. For example, the sleeve 104 of apparatus 100 may be configured to include one or more features of the receiving portion 238, such as, but not limited to, the flange 270 and receiving slots 274, of the sleeve 204. The various embodiments described above are provided by way of illustration only and should not be construed to limit the claims attached hereto. Those skilled in the art will readily recognize various modifications and changes that may be made without following the example embodiments and applications illustrated and described herein, and without departing from the spirit and scope of the following claims.

What is claimed is:

1. An injection apparatus comprising:
a syringe housed within a sleeve, the syringe comprising a barrel, a needle mounted to an end of the barrel, a plunger, and a seal slidably mounted in the barrel;
a housing; and
the sleeve having an arm that extends from the sleeve and is coupled to the housing such that the sleeve is configured to rotate within the housing and guide the needle to a target site;
wherein the housing comprises:
a protruded member extending upwardly from a planar member of the housing; and
the protruded member comprising a cavity sized to receive the sleeve therein;
wherein:
at least one side wall of the protruded member comprises a hollow sized to receive a rotation button disposed on a distal end of the arm of the sleeve, and
the housing and sleeve are rotatably coupled to one another via the rotation button positioned within the hollow;
wherein:
the hollow includes one or more rotation recesses sized to receive a detent protruding from an outer surface of the rotation button, and
a position of a rotation recess corresponds to an insertion position of the sleeve.

2. The injection apparatus of claim 1, wherein the housing further comprises one or more rigid reinforcing members, the reinforcing member extending between a side wall of the protruded member and an upper surface of the planar member.

3. The injection apparatus of claim 1, wherein the planar member comprises curved outer ends disposed on opposite sides of the protruded member.

4. The injection apparatus of claim 1, wherein a contact portion of the planar member comprises a smooth surface defining an opening that forms a channel with the cavity, the opening sized to allow the needle to pass therethrough.

5. The injection apparatus of claim 1, wherein the sleeve comprises a second arm extending from the sleeve and positioned to engage the housing to fix the sleeve and syringe with respect to the housing upon rotation of the sleeve to an engagement position.

6. The injection apparatus of claim 5, wherein the second arm is a flexible member having a hook on a distal end of the second arm and a contact portion extending away from the hook and disposed to allow a user to assert pressure against the contact portion to bend the flexible member.

7. The injection apparatus of claim 6, wherein in a preparation position, the hook is engaged with a top portion of a bridge of the housing such that the needle is positioned within the housing and the sleeve is inhibited from rotating towards a bottom of the housing.

8. The injection apparatus of claim 6, wherein in an insertion position, the hook is engaged with a bottom portion of a bridge of the housing such that the needle is positioned outside of a bottom of the housing and the sleeve is inhibited from rotating towards a top of the housing.

9. The injection apparatus of claim 1, wherein an end of the sleeve comprises flexible interlocking members that are positioned on opposing sides of the sleeve and are configured to interlock with a flange of the barrel.

10. The injection apparatus of claim 1, wherein:
the sleeve further comprises:
- a receiving portion having a rigid channel disposed between a first end and a second end, the arm being positioned on the first end of the receiving portion; and
- a connection portion coupled to the second end of the receiving portion at a proximal end of the connection portion, the connection portion comprising a flange having receiving slots disposed on opposite sides of the flange, the receiving slots configured to receive a respective portions of a barrel flange of the syringe.

11. An injection apparatus comprising:
a housing having a protruded member extending upwardly from a planar member of the housing, the protruded member comprising a cavity sized to receive a sleeve therein; and
the sleeve being configured to receive a syringe and having an arm that extends from the sleeve and is rotatably coupled to the housing such that the sleeve is rotatable within the housing to guide a needle of the syringe to a target site;
wherein:
at least one side wall of the protruded member comprises a hollow sized to receive a rotation button disposed on a distal end of the arm of the sleeve, and
the housing and the sleeve are rotatably coupled to one another via the rotation button positioned within the hollow;
wherein:
the hollow includes one or more rotation recesses sized to receive a detent protruding from an outer surface of the rotation button, and
a position of a rotation recess corresponds to an insertion position of the sleeve.

12. The injection apparatus of claim 11, wherein the housing further comprises one or more rigid reinforcing members, the reinforcing member extending between a side wall of the protruded member and an upper surface of the planar member.

13. The injection apparatus of claim 12, wherein a contact portion of the planar member comprises a smooth surface defining an opening that forms a channel with the cavity, the opening sized to allow the needle to pass therethrough.

14. The injection apparatus of claim 11, wherein the sleeve comprises a second arm extending from the sleeve and positioned to engage the housing to fix the sleeve and syringe with respect to the housing upon rotation of the sleeve to an engagement position.

15. The injection apparatus of claim 11, wherein:
in a first position, the sleeve is configured within the housing to locate the needle of the received syringe within the housing, and
in a second position, the sleeve is configured within the housing to locate at least a portion of the needle is positioned outside of the housing.

* * * * *